(12) United States Patent
Melcher et al.

(10) Patent No.: US 6,924,109 B2
(45) Date of Patent: Aug. 2, 2005

(54) HIGH-THROUGHPUT TRANSCRIPTOME AND FUNCTIONAL VALIDATION ANALYSIS

(75) Inventors: Thorsten Melcher, San Francisco, CA (US); Keith Charles McFarland, Davis, CA (US); Li Gan, San Francisco, CA (US); Shiming Ye, Albany, CA (US); Mirella Gonzalez-Zulueta, Pacifica, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 196 days.

(21) Appl. No.: 10/116,437

(22) Filed: Apr. 3, 2002

(65) Prior Publication Data

US 2003/0082570 A1 May 1, 2003

Related U.S. Application Data

(63) Continuation-in-part of application No. 10/027,807, filed on Oct. 19, 2001, which is a continuation-in-part of application No. 09/627,362, filed on Jul. 28, 2000, now abandoned
(60) Provisional application No. 60/146,640, filed on Jul. 30, 1999.

(51) Int. Cl.[7] .......................... C12Q 1/68; C12N 15/00; C12N 15/63; C12N 1/20; C07H 21/04
(52) U.S. Cl. .................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2, 435/325; 536/24.3; 935/6; 436/518; 424/94.67

(56) References Cited

U.S. PATENT DOCUMENTS

| | | | | | |
|---|---|---|---|---|---|
| 5,690,932 | A | * | 11/1997 | Naggert | 424/94.67 |
| 5,846,721 | A | * | 12/1998 | Soares | 435/6 |
| 6,028,248 | A | | 2/2000 | Somerville et al. | |
| 6,074,872 | A | * | 6/2000 | Sutcliffe | 435/325 |
| 6,197,557 | B1 | * | 3/2001 | Makarov | 435/91.2 |
| 6,242,253 | B1 | * | 6/2001 | Karin | 435/325 |
| 6,506,559 | B1 | * | 1/2003 | Fire | 435/6 |

FOREIGN PATENT DOCUMENTS

WO  WO 00/44914  8/2000

OTHER PUBLICATIONS

Paddison et al., Stable Suppression of Gene Expression by RNAI in Mammalian Cells, PNAS, (2002), vol. 99, No. 3, pp. 1443–1448.

* cited by examiner

*Primary Examiner*—Jeffrey Fredman
*Assistant Examiner*—Arun Chakrabarti
(74) *Attorney, Agent, or Firm*—Pamela J. Sherwood; Bozicevic, Field & Francis LLP; Rebecca D. Taylor

(57) ABSTRACT

Methods for correlating genes and gene function are provided. Such methods generally involve selecting a candidate gene that appears to be correlated with a particular cellular state or activity and then validating the role of the candidate gene in establishment of such a cellular state or activity. Certain methods utilize RNA interference techniques in the validation process.

21 Claims, 13 Drawing Sheets

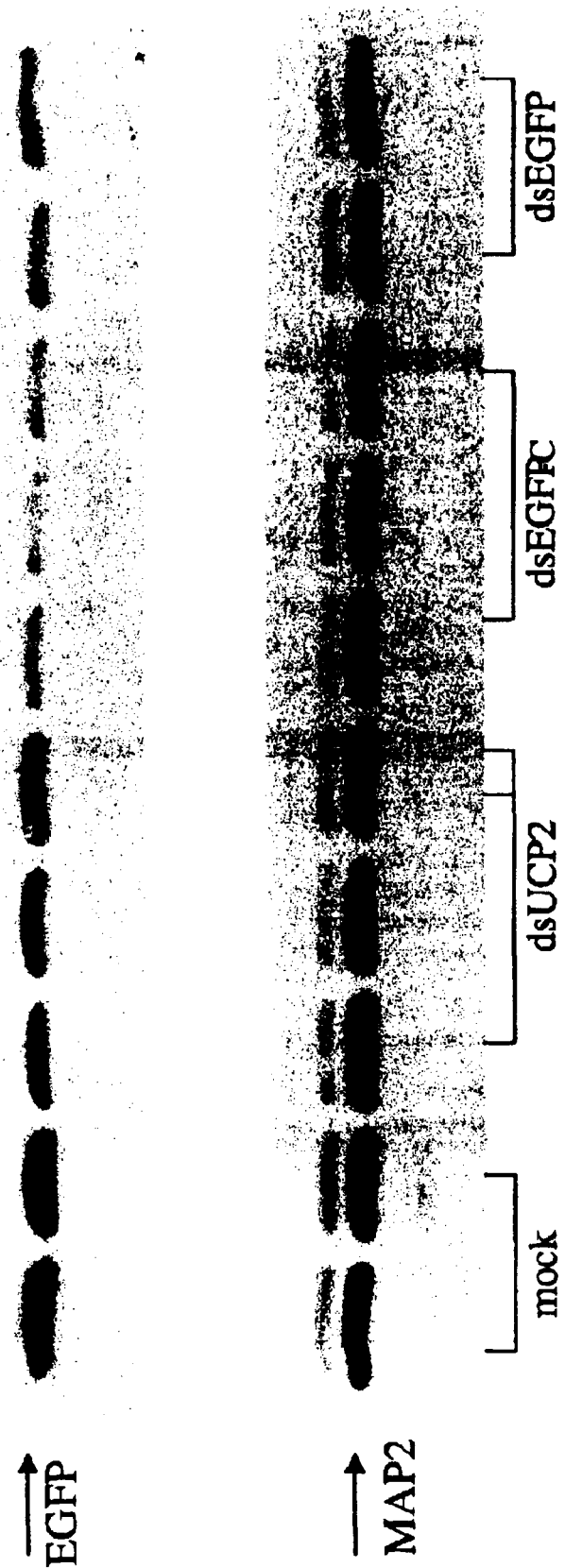

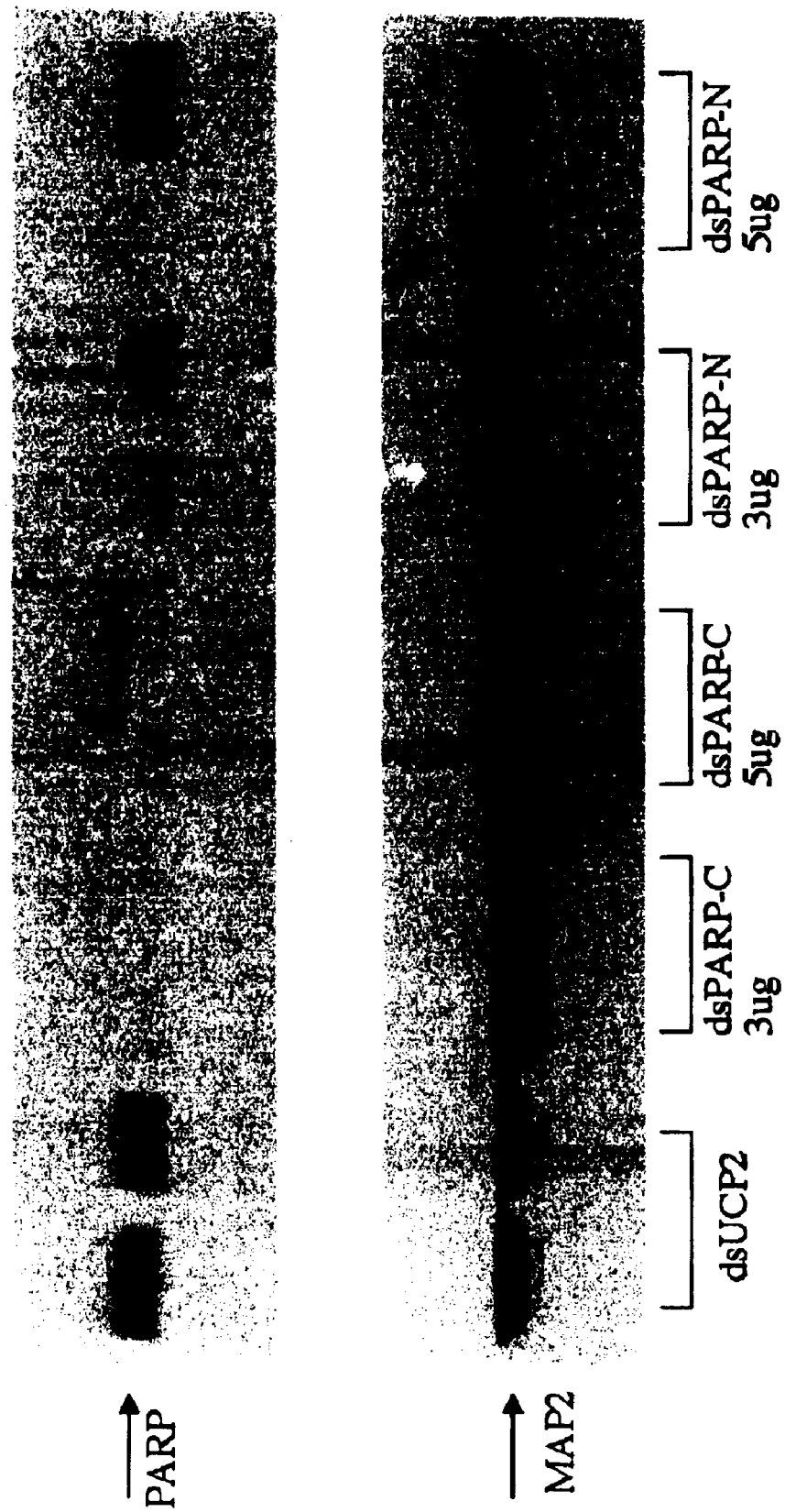

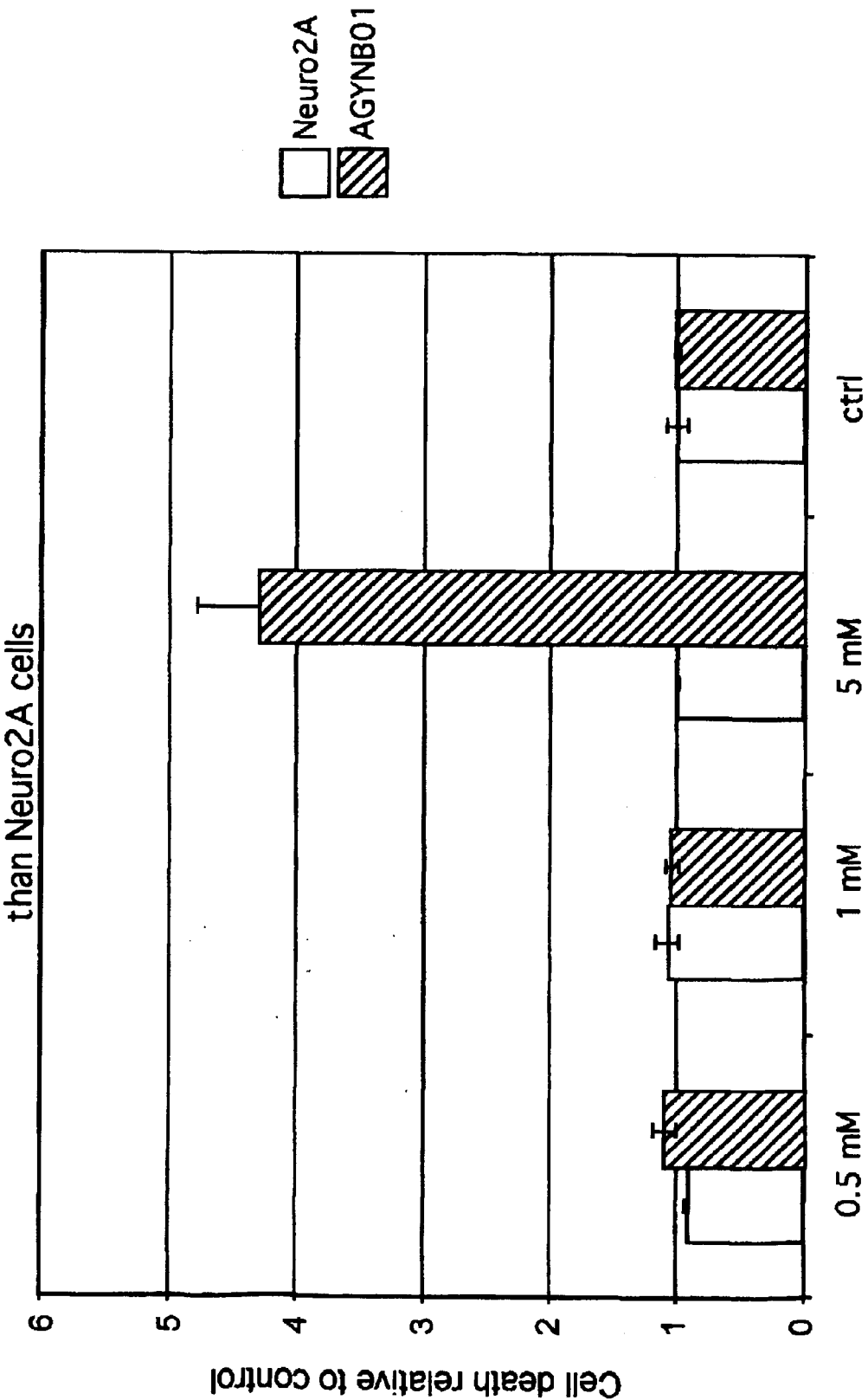

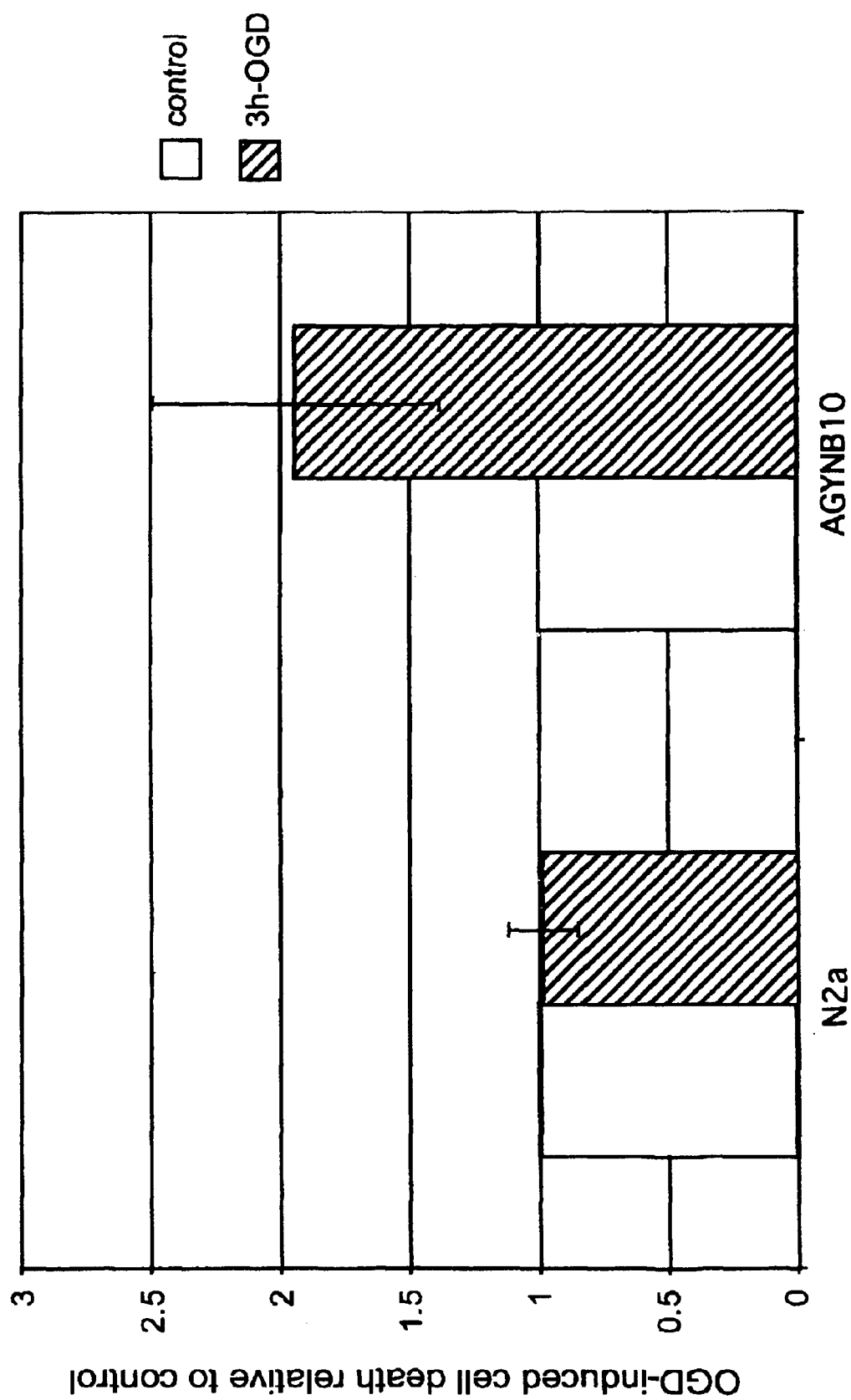

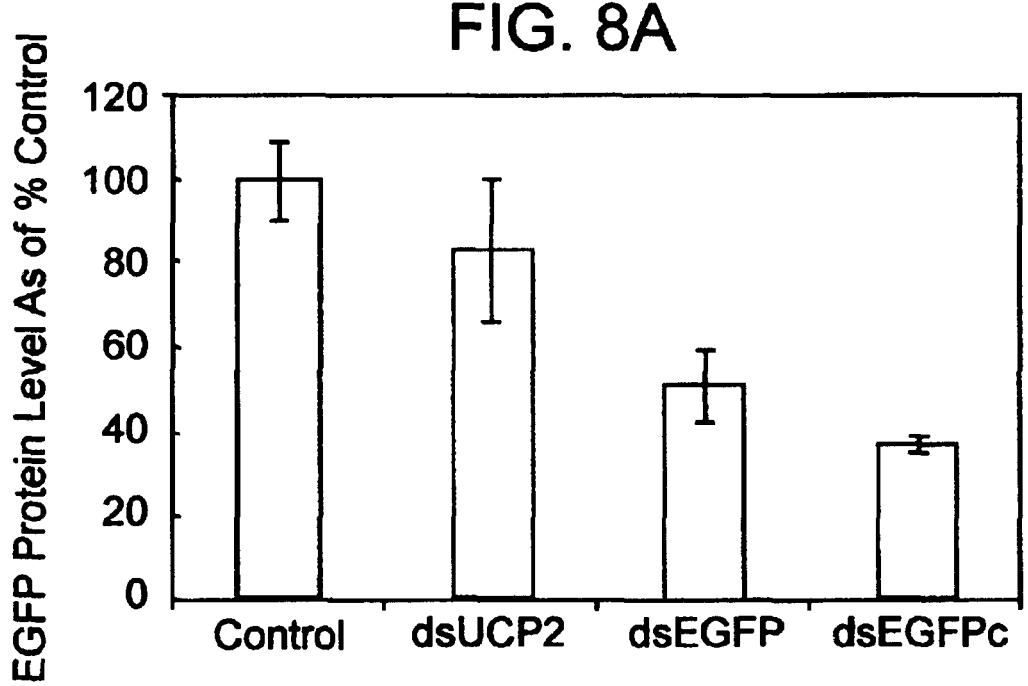
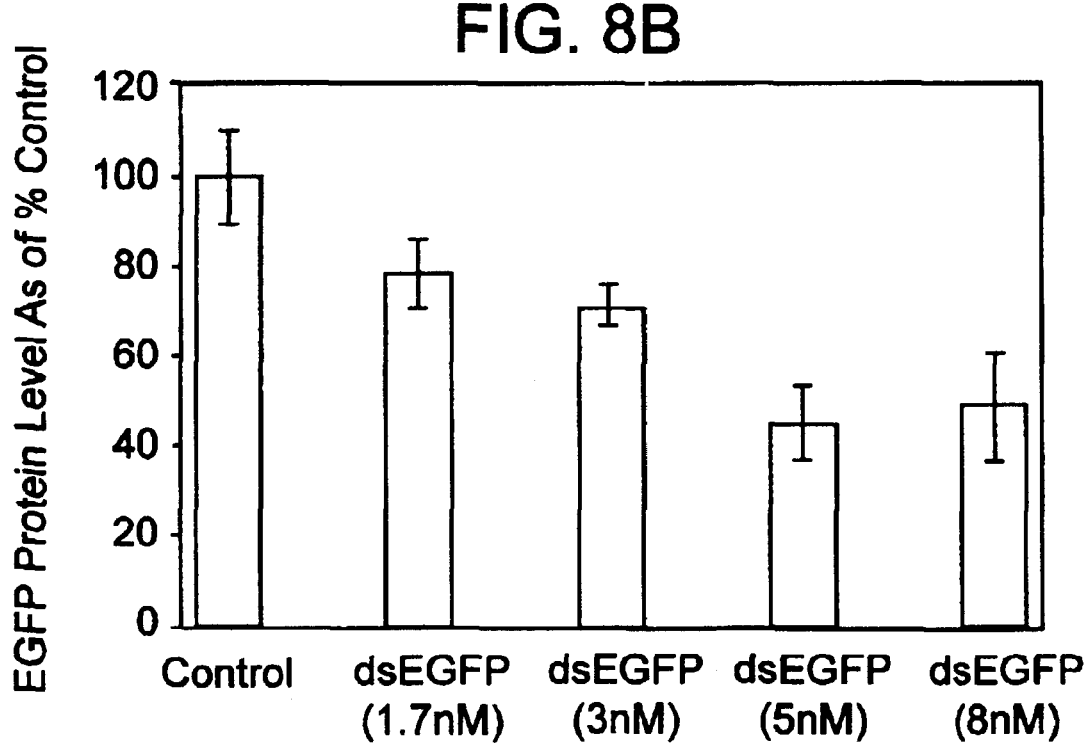

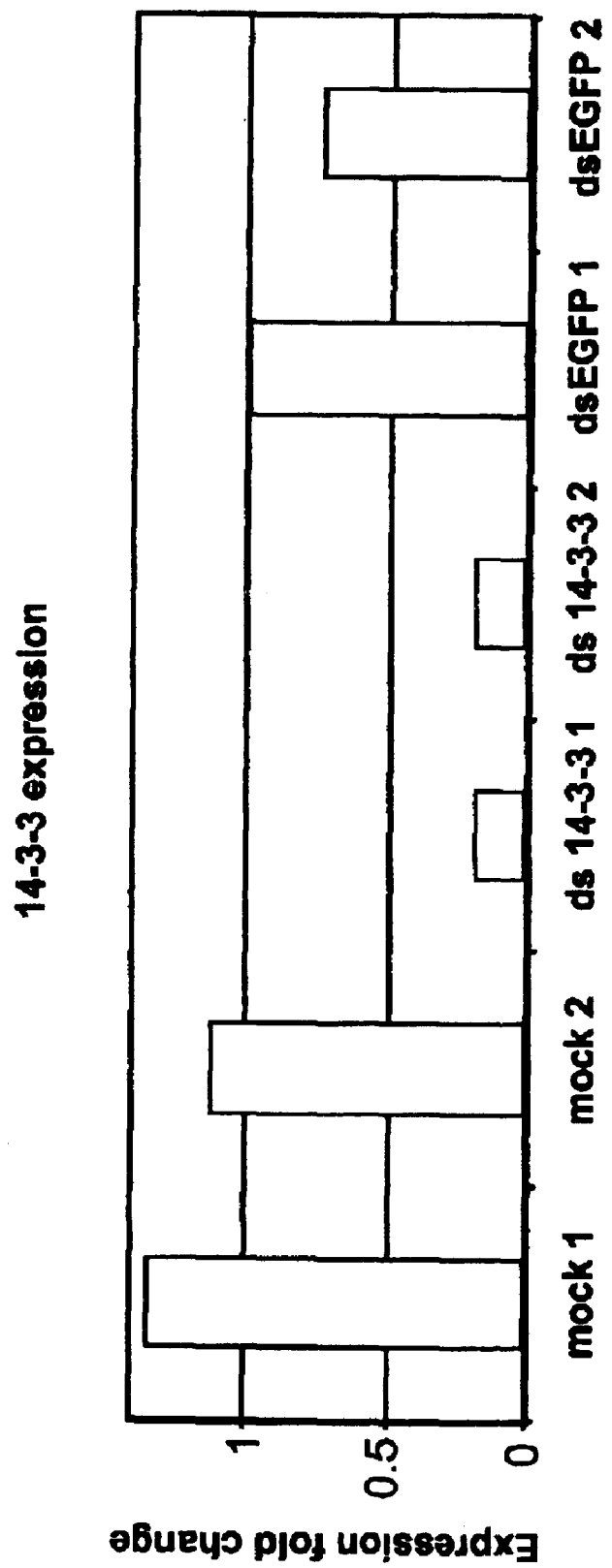

SEQUENCE LISTING

<160> NUMBER OF SEQ ID NOS: 41

<210> SEQ ID NO 1
<211> LENGTH: 44
<212> TYPE: DNA
<213> ORGANISM: Artificial Sequence
<220> FEATURE:
<223> OTHER INFORMATION: Primers

<400> SEQUENCE: 1
ctaatacgac tcactatagg gctcgagcgg ccgcccgggc aggt     44

<210> SEQ ID NO 2
<211> LENGTH: 42
<212> TYPE: DNA
<213> ORGANISM: Artificial Sequence
<220> FEATURE:
<223> OTHER INFORMATION: Primers

<400> SEQUENCE: 2
ctaatacgac tcactatagg gcagcgtggt cgcggccgag gt     42

<210> SEQ ID NO 3
<211> LENGTH: 22
<212> TYPE: DNA
<213> ORGANISM: Artificial Sequence
<220> FEATURE:
<223> OTHER INFORMATION: Primers

<400> SEQUENCE: 3

-continued ctaatacgac tcactatagg gc                                              22

<210> SEQ ID NO 4
<211> LENGTH: 10
<212> TYPE: DNA
<213> ORGANISM: Artificial Sequence
<220> FEATURE:
<223> OTHER INFORMATION: Primers

<400> SEQUENCE: 4
acctgcccgg                                                            10

<210> SEQ ID NO 5
<211> LENGTH: 10
<212> TYPE: DNA
<213> ORGANISM: Artificial Sequence
<220> FEATURE:
<223> OTHER INFORMATION: Primers

<400> SEQUENCE: 5
acctcggccg                                                            10

<210> SEQ ID NO 6
<211> LENGTH: 22
<212> TYPE: DNA
<213> ORGANISM: Artificial Sequence
<220> FEATURE:
<223> OTHER INFORMATION: Primers

<400> SEQUENCE: 6
tcgagcggcc gcccgggcag gt                                              22

<210> SEQ ID NO 7
<211> LENGTH: 20
<212> TYPE: DNA
<213> ORGANISM: Artificial Sequence
<220> FEATURE:
<223> OTHER INFORMATION: Primers

<400> SEQUENCE: 7
agcgtggtcg cggccgaggt                                                 20

<210> SEQ ID NO 8
<211> LENGTH: 22
<212> TYPE: DNA
<213> ORGANISM: Artificial Sequence
<220> FEATURE:
<223> OTHER INFORMATION: Primers

<400> SEQUENCE: 8
tcgagcggcc gcccgggcag gt                                              22

<210> SEQ ID NO 9
<211> LENGTH: 10
<212> TYPE: DNA
<213> ORGANISM: Artificial Sequence
<220> FEATURE:
<223> OTHER INFORMATION: Primers

<400> SEQUENCE: 9
acctgcccgg                                                            10

<210> SEQ ID NO 10
<211> LENGTH: 20
<212> TYPE: DNA
<213> ORGANISM: Artificial Sequence -continued

```
<220> FEATURE:
<223> OTHER INFORMATION: Primers

<400> SEQUENCE: 10
agcgtggtcg cggccgaggt                                           20

<210> SEQ ID NO 11
<211> LENGTH: 10
<212> TYPE: DNA
<213> ORGANISM: Artificial Sequence
<220> FEATURE:
<223> OTHER INFORMATION: Primers

<400> SEQUENCE: 11
acctcggccg                                                      10

<210> SEQ ID NO 12
<211> LENGTH: 22
<212> TYPE: DNA
<213> ORGANISM: Artificial Sequence
<220> FEATURE:
<223> OTHER INFORMATION: Primers

<400> SEQUENCE: 12
tcgagcggcc gcccgggcag gt                                        22

<210> SEQ ID NO 13
<211> LENGTH: 20
<212> TYPE: DNA
<213> ORGANISM: Artificial Sequence
<220> FEATURE:
<223> OTHER INFORMATION: Primers

<400> SEQUENCE: 13
agcgtggtcg cggccgaggt                                           20

<210> SEQ ID NO 14
<211> LENGTH: 22
<212> TYPE: DNA
<213> ORGANISM: Artificial Sequence
<220> FEATURE:
<223> OTHER INFORMATION: Primers

<400> SEQUENCE: 14
ctaatacgac tcactatagg gc                                        22

<210> SEQ ID NO 15
<211> LENGTH: 22
<212> TYPE: DNA
<213> ORGANISM: Artificial Sequence
<220> FEATURE:
<223> OTHER INFORMATION: Primers

<400> SEQUENCE: 15
tcgagcggcc gcccgggcag gt                                        22

<210> SEQ ID NO 16
<211> LENGTH: 20
<212> TYPE: DNA
<213> ORGANISM: Artificial Sequence
<220> FEATURE:
<223> OTHER INFORMATION: Primers

<400> SEQUENCE: 16
agcgtggtcg cggccgaggt                                           20
```

```
<210> SEQ ID NO 17
<211> LENGTH: 24
<212> TYPE: DNA
<213> ORGANISM: Artificial Sequence
<220> FEATURE:
<223> OTHER INFORMATION: Primers

<400> SEQUENCE: 17
atggtgagca agggcgagga gctg                                           24

<210> SEQ ID NO 18
<211> LENGTH: 24
<212> TYPE: DNA
<213> ORGANISM: Artificial Sequence
<220> FEATURE:
<223> OTHER INFORMATION: Primers

<400> SEQUENCE: 18
tctgagtccg gacttgtaca gctc                                           24

<210> SEQ ID NO 19
<211> LENGTH: 22
<212> TYPE: DNA
<213> ORGANISM: Artificial Sequence
<220> FEATURE:
<223> OTHER INFORMATION: Primers

<400> SEQUENCE: 19
gtctccacca cccagctcca tg                                             22

<210> SEQ ID NO 20
<211> LENGTH: 22
<212> TYPE: DNA
<213> ORGANISM: Artificial Sequence
<220> FEATURE:
<223> OTHER INFORMATION: Primers

<400> SEQUENCE: 20
agatgctgac gagggtactg ca                                             22

<210> SEQ ID NO 21
<211> LENGTH: 24
<212> TYPE: DNA
<213> ORGANISM: Artificial Sequence
<220> FEATURE:
<223> OTHER INFORMATION: Primers

<400> SEQUENCE: 21
tggagaacaa caaaacctca gtgg                                           24

<210> SEQ ID NO 22
<211> LENGTH: 24
<212> TYPE: DNA
<213> ORGANISM: Artificial Sequence
<220> FEATURE:
<223> OTHER INFORMATION: Primers

<400> SEQUENCE: 22
ctgttaacgc gagtgagaat gtgc                                           24

<210> SEQ ID NO 23
<211> LENGTH: 22
<212> TYPE: DNA
<213> ORGANISM: Artificial Sequence
<220> FEATURE:
<223> OTHER INFORMATION: Primers
```

```
<400> SEQUENCE: 23
acctcactgc atggacgatc tg                                        22

<210> SEQ ID NO 24
<211> LENGTH: 22
<212> TYPE: DNA
<213> ORGANISM: Artificial Sequence
<220> FEATURE:
<223> OTHER INFORMATION: Primers

<400> SEQUENCE: 24
gcagttcagg gcaaaggact tc                                        22

<210> SEQ ID NO 25
<211> LENGTH: 20
<212> TYPE: DNA
<213> ORGANISM: Artificial Sequence
<220> FEATURE:
<223> OTHER INFORMATION: Primers

<400> SEQUENCE: 25
cggcaaatgg ttgaaactga                                           20

<210> SEQ ID NO 26
<211> LENGTH: 21
<212> TYPE: DNA
<213> ORGANISM: Artificial Sequence
<220> FEATURE:
<223> OTHER INFORMATION: Primers

<400> SEQUENCE: 26
cctgcagcgc ttctttattc t                                         21

<210> SEQ ID NO 27
<211> LENGTH: 20
<212> TYPE: DNA
<213> ORGANISM: Artificial Sequence
<220> FEATURE:
<223> OTHER INFORMATION: Primers

<400> SEQUENCE: 27
gcaggagagg cccacgttct                                           20

<210> SEQ ID NO 28
<211> LENGTH: 21
<212> TYPE: DNA
<213> ORGANISM: Artificial Sequence
<220> FEATURE:
<223> OTHER INFORMATION: Primers

<400> SEQUENCE: 28
catcatcagt gtgccgagcc a                                         21

<210> SEQ ID NO 29
<211> LENGTH: 22
<212> TYPE: DNA
<213> ORGANISM: Artificial Sequence
<220> FEATURE:
<223> OTHER INFORMATION: Primers

<400> SEQUENCE: 29
gccagaccac aacaggaagc at                                        22

<210> SEQ ID NO 30
```

<210> SEQ ID NO 30
<211> LENGTH: 20
<212> TYPE: DNA
<213> ORGANISM: Artificial Sequence
<220> FEATURE:
<223> OTHER INFORMATION: Primers

<400> SEQUENCE: 30
gtacgcgcac aagctagaat                                            20

<210> SEQ ID NO 31
<211> LENGTH: 21
<212> TYPE: DNA
<213> ORGANISM: Artificial Sequence
<220> FEATURE:
<223> OTHER INFORMATION: Primers

<400> SEQUENCE: 31
aaagtggagt ccagggagaa g                                          21

<210> SEQ ID NO 32
<211> LENGTH: 20
<212> TYPE: DNA
<213> ORGANISM: Artificial Sequence
<220> FEATURE:
<223> OTHER INFORMATION: Primers

<400> SEQUENCE: 32
ggtggtcaaa ggttggaagt                                            20

<210> SEQ ID NO 33
<211> LENGTH: 22
<212> TYPE: DNA
<213> ORGANISM: Artificial Sequence
<220> FEATURE:
<223> OTHER INFORMATION: Primers

<400> SEQUENCE: 33
ccattacgtg aggagtcagt tc                                         22

<210> SEQ ID NO 34
<211> LENGTH: 19
<212> TYPE: DNA
<213> ORGANISM: Artificial Sequence
<220> FEATURE:
<223> OTHER INFORMATION: Primers

<400> SEQUENCE: 34
gcgtaaacgc ttcgagatg                                             19

<210> SEQ ID NO 35
<211> LENGTH: 21
<212> TYPE: DNA
<213> ORGANISM: Artificial Sequence
<220> FEATURE:
<223> OTHER INFORMATION: Primers

<400> SEQUENCE: 35
agtagactgg cccttcttgg t                                          21

<210> SEQ ID NO 36
<211> LENGTH: 22
<212> TYPE: DNA
<213> ORGANISM: Artificial Sequence
<220> FEATURE:
<223> OTHER INFORMATION: Primers

<400> SEQUENCE: 36

```
ctggccagtg gtaaatgtac tg                                          22

<210> SEQ ID NO 37
<211> LENGTH: 20
<212> TYPE: DNA
<213> ORGANISM: Artificial Sequence
<220> FEATURE:
<223> OTHER INFORMATION: Primers

<400> SEQUENCE: 37
ctctgccttt tgctgtcaga                                             20

<210> SEQ ID NO 38
<211> LENGTH: 19
<212> TYPE: DNA
<213> ORGANISM: Artificial Sequence
<220> FEATURE:
<223> OTHER INFORMATION: Primers

<400> SEQUENCE: 38
cgctgtggac ctcagacat                                              19

<210> SEQ ID NO 39
<211> LENGTH: 22
<212> TYPE: DNA
<213> ORGANISM: Artificial Sequence
<220> FEATURE:
<223> OTHER INFORMATION: Primers

<400> SEQUENCE: 39
ggggtagtca gagatggttt ct                                          22

<210> SEQ ID NO 40
<211> LENGTH: 22
<212> TYPE: DNA
<213> ORGANISM: Artificial Sequence
<220> FEATURE:
<223> OTHER INFORMATION: Primers

<400> SEQUENCE: 40
gtggaagagc ctgacctatg at                                          22

<210> SEQ ID NO 41
<211> LENGTH: 22
<212> TYPE: DNA
<213> ORGANISM: Artificial Sequence
<220> FEATURE:
<223> OTHER INFORMATION: Primers

<400> SEQUENCE: 41
cccctcacag tgaagtgaga ta                                          22
```

HIGH-THROUGHPUT TRANSCRIPTOME AND FUNCTIONAL VALIDATION ANALYSIS

CROSS-REFERENCE TO RELATED APPLICATIONS

This application is a continuation-in-part application of U.S. patent application Ser. No. 10/027,807, filed Oct. 19, 2001, which is a continuation-in-part of U.S. patent application Ser. No. 09/627,362, filed Jul. 28, 2000 abandoned, which claims the benefit of U.S. Provisional Application No. 60/146,640, filed Jul. 30, 1999, all of which are incorporated herein in their entirety for all purposes.

BACKGROUND

It is estimated that while over 100,000 genes are expressed by a mammalian genome, only a fraction are expressed in any particular cell or tissue. Gene expression patterns, especially as reflected in the abundance of mRNAs, vary according to cell or tissue type, with developmental or metabolic state, in response to insult or injury, and as a consequence of other genetic and environmental factors. Moreover, the pattern of expression changes in a dynamic fashion over time with changes in cell state and environment. The term "transcriptome" has been coined to describe the set of all genes expressed, at any given time, under defined conditions in a given tissue (Velculescu et al., 1997, Cell 88:243–51).

The detection of changes to the transcriptome can provide useful information regarding the identity of genes and gene products important in development, drug response, and, particularly, human disease processes. However, methods now used for identifying changes in the transcriptome suffer from a variety of deficiencies, e.g., they are expensive, require relatively large quantities of starting material, and/or do not efficiently identify low abundance transcripts important in mediating cell processes.

While a change in the expression of a particular gene between different cell states is evidence that the gene may be responsible for the difference in cell states, it would be preferable that the putative role assigned to the gene be validated. Such validation ideally would involve an assay system in which one can interrogate what effect, if any, modulation of expression of the gene has on a cellular state or cellular activity. If modulation of expression was found to be correlated with a change in cellular state or activity, this would substantiate the putative role for the gene. Thus, there remains a need for high throughput methods for first identifying genes that appear to play a role in a particular cellular state or activity and then validating that the gene does in fact have such a role.

BRIEF SUMMARY OF THE INVENTION

One aspect of the present invention provides a method for identifying and producing an active double-stranded RNA (dsRNA) which attenuates a desired gene expression in a cell. In one particular embodiment, the method for identifying and producing an active dsRNA comprises: (a) producing a plurality of cDNA, wherein each cDNA comprises at least a portion of a gene that is expressed in a cell; (b) producing a candidate dsRNA from at least one of the cDNAs; (c) introducing the candidate dsRNA into a reference cell having a gene expression similar to the cell in step (a); and (d) identifying an active dsRNA by determining whether the candidate dsRNA attenuates a desired gene expression in the reference cell.

Moreover, methods of the present invention can also include producing the identified active dsRNA from the corresponding cDNA of step (a). Since methods of the present invention provide a library, preferably a comprehensive library, of cDNA, once the active dsRNA has been identified it can be readily synthesized by transcription of the corresponding cDNA. Therefore, methods of the present invention do not require conventional chemical oligonucleotide synthesis and/or availability of known gene sequences to produce the active dsRNA.

Identification of the active dsRNA include selecting a candidate gene and identifying whether the dsRNA of at least a portion of the candidate gene is an active dsRNA by determining whether modulation of expression of the candidate gene by dsRNA in a reference cell has a functional effect in the reference cell. The candidate gene is a gene that is expressed in a test cell and/or a control cell, and/or is expressed at a detectably different level with respect to the test cell and the control cell. The candidate gene can be an endogenous gene of the reference cell, or it can be present in the reference cell as an extrachromosomal gene. The test cell and control cell differ with respect to a particular cellular characteristic of interest. The active dsRNA alters a cellular activity or a cellular state in the reference cell by modulating the expression of the candidate gene.

Active dsRNA can be identified by a variety of methods, including by introducing the candidate dsRNA into the reference cell and detecting an alteration in a cellular activity or a cellular state in the reference cell. The alteration in a cellular activity or a cellular state in the reference cell indicates that the candidate gene plays a functional role in the reference cell and that the candidate dsRNA is an active dsRNA. Preferably, the candidate dsRNA is selected such that it is substantially identical to at least a part of the candidate gene.

In one embodiment, the cellular characteristic is cell health, the test cell is a diseased cell and the control cell is a healthy cell, and the candidate gene is potentially correlated with a disease.

In another embodiment, the cellular characteristic is stage of development and the test cell and the control cell are at different stages of development, and the candidate gene is potentially correlated with mediating the change between the different stages of development.

In yet another embodiment, the cellular characteristic is cellular differentiation and the candidate gene is potentially correlated with controlling cellular differentiation.

Preferably, the plurality of cDNA, which is used to synthesize dsRNA, is produced from at least one mRNA which is isolated from the cell. The isolated mRNA is then reverse transcribed by any of the methods conventionally known to one skilled in the art to produce the cDNA. Typically, the cDNA is then digested with one or more, preferably two, restriction enzymes to produce a plurality of similar length cDNAs. In this manner, a more comprehensive cDNA library is provided. In one particular embodiment of the present invention, the restriction enzyme is selected from the group consisting of Dpn1 and Rsa1. A plasmid or PCR fragment is then generated from the digested cDNAs by any of the conventional methods known to one skilled in the art. And the candidate dsRNA is the produced by transcription of the plasmid or the PCR fragment.

In another embodiment, the cDNA is produced from all mRNAs that are isolated from the control cell. This provides a comprehensive cDNA library which comprises at least a portion of substantially all genes that are actively expressed in the cell.

Another aspect of the present invention provides a method for identifying and validating activity of an active dsRNA which attenuates a desired gene expression in a cell. The method generally comprises producing a candidate dsRNA, introducing the candidate dsRNA into a reference cell and identifying whether the candidate dsRNA is an active dsRNA by detecting an alteration in a cellular activity or a cellular state in the reference cell.

Yet another aspect of the present invention provides a high-through put method for correlating genes and gene function, said method comprising: (a) producing a plurality of candidate dsRNAs from a plurality of cDNAs of a control cell such that each candidate dsRNA comprises at least a portion of a gene that is expressed in the control cell; (b) introducing each of the candidate dsRNA into a plurality of separate reference cell each having a gene expression similar to the control cell in step (a); and (c) identifying which candidate dsRNA is an active dsRNA by detecting an alteration in a cellular activity or a cellular state in the reference cell, desired alteration indicating that the gene corresponding to the candidate dsRNA plays a functional role in the reference cell.

In one embodiment, the plurality of cDNAs is produced from a plurality of mRNAs as described herein. Preferably, each candidate dsRNA is substantially identical to at least a portion of the candidate gene.

Detecting an alteration in a cellular activity or a cellular state in the reference cell can involve a variety of methods. For example, one can detect modulation of ligand binding to a protein, detect a change in phenotype or determine whether the protein encoded by the candidate gene binds to another protein to form a complex that can be coimmunoprecipitated. Detecting a change in phenotype is particularly useful when the reference cell is a part of an organism. In addition, detecting an alteration in a cellular activity or a cellular state in the reference cell can involve determining whether interference with expression of the candidate gene in the reference cell is correlated with alteration of a cellular activity or cellular state. Interference can be achieved by introducing a double-stranded RNA into the reference cell that can specifically hybridize to the candidate gene.

The candidate gene can be selected from a normalized library prepared from cells of the same type as the test cell or the control cell. In one particular embodiment, the candidate gene is present in low abundance in the normalized library.

In another embodiment, the candidate gene is a differentially expressed gene selected from a subtracted library that is enriched for genes that are differentially expressed with respect to the test cell and the control cell. Preferably, the subtracted library is also normalized and the candidate gene is one of the genes that is both present in low abundance and differentially expressed in the subtracted and normalized library.

In one particular embodiment of the present invention, the candidate gene is selected by a method comprising: (i) preparing (A) a tester-normalized cDNA library which is a normalized library prepared from test cells; (B) a driver-normalized cDNA library which is a normalized library prepared from control cells; (C) a tester-subtracted cDNA library which is enriched in one or more genes that are up-regulated with respect to the test cell and the control cell, and (D) a driver-subtracted cDNA library which is enriched in one or more genes that are down-regulated with respect to the test cell and the control cell; and (ii) identifying one or more clones from the normalized libraries and/or the subtracted libraries, wherein the candidate gene is one of the clones identified.

In one embodiment, identification of one or more clones from the normalized libraries comprises: (A) contacting clones from the tester-normalized cDNA library with labeled probes derived from mRNA from test cells and contacting clones from the driver-normalized cDNA library with labeled probes derived from mRNA from control cells under conditions whereby probes specifically hybridize with complementary clones to form a first set of hybridization complexes; and (B) detecting at least one hybridization complex from the first set of hybridization complexes to identify a clone from one of the normalized libraries which is present in low abundance.

In another embodiment, identification of one or more clones from the normalized libraries comprises: (A) contacting clones from the tester-subtracted cDNA library and contacting clones from the driver-subtracted cDNA library with a population of labeled probes under conditions whereby probes from the population of probes specifically hybridize with complementary clones to form a second set of hybridization complexes, and wherein the population of labeled probes is derived from mRNA from test cells and control cells; and (B) detecting at least one hybridization complex from the second set of hybridization complexes to identify a clone from one of the subtracted libraries which is differentially expressed above a threshold level with respect to the subtracted libraries.

Methods of the present invention can be used with a wide variety of cells and cell types. For example, in one embodiment the test cell is obtained from a mammal that has had a stroke or is at risk for stroke. In another embodiment, the test cell is obtained from a mammal that has neurological disorders or develop phenotypes mimicking human neurological disorders.

The reference cell can be part of a cell culture, a tissue, part of an organism, an embryo, neural, glial cell or a neuroblastoma cell. The reference cell can be a mammalian cell. Preferably, the reference cell is human cell or a model system which is useful for investigating a variety of human diseases and/or illnesses.

In one embodiment, the reference cell is useful as a model system for investigating neurological disorders in humans. In one particular embodiment, the reference cell has increased sensitivity to N-methyl-D-aspartate, β-amyloid, peroxide, oxygen-glucose deprivation, or combinations thereof. In such cases, the detecting step can comprises detecting a decrease in cellular sensitivity to N-methyl-D-aspartate, β-amyloid, peroxide, oxygen-glucose deprivation, or combinations thereof.

BRIEF DESCRIPTION OF THE FIGURES

FIG. 5. A Western Blot showing inhibition of expression of eGFP (enhanced Green Fluorescent Protein) by eGFP dsRNA in a neuroblastoma cell line (AGYNB-010) harboring a plasmid encoding for eGFP. The blot shows inhibition of eGFP expression for cells transfected with eGFP dsRNA (i.e., dsRNA corresponding to the entire eGFP coding region; lanes 9 and 10) and for cells transfected with eGFP dsRNA from the C-terminus (dsEGFP-C; lanes 6–8). Untransfected cells (mock cells; lanes 1–2) and cells transfected with UCP-2 dsRNA (dsUCP2; lanes 3–5) served as controls and show little or no inhibition of eGFP expression. Anti-MAP2 was used to assure equal loading.

FIG. 6A. A Western Blot showing inhibition of endogenous PARP by PARP dsRNA. Inhibition of endogenous PARP expression is observed for neuroblastoma cells (AGYNB-010) transfected with PARP dsRNA prepared from the C-terminus of PARP (dsPARP-C; lanes 3–6) or PARP dsRNA prepared from the N-terminus of PARP (dsPARP-N; lanes 7–10). Control cells transfected with UCP-2 dsRNA, in contrast, still express endogenous PARP (lanes 1–2). Anti-MAP2 was used to assure equal loading.

FIGS. 6B and 6C show views of neuroblastoma cells (AGYNB-010 cells) subjected to 6 hours of OGD. Cell viability was assayed by staining with a fluorescent dye that preferentially stains healthy cells rather than dead cells. Cells transfected with dsPARP 3 hours after initiation of OGD show significantly less cell death (FIG. 6C) as compared to control cells transfected with dsEGFP (FIG. 6B). FIG. 6D is a chart showing that AGYNB-010 cells transfected with dsPARP are rescued from cell death following 3 hours of OGD, whereas control cells that are either untransfected (mock cells) or transfected with dsEGFP show significant cell death after 6 hours of OGD.

FIGS. 7A–7C. Charts showing sensitivity of the AGYNB-010 neuroblastoma cell line to β-amyloid (FIG. 7A), N-methyl-D-aspartate (NMDA) (FIG. 7B) and oxygen glucose deprivation (OGD) (FIG. 7C).

FIGS. 8A and 8B are graphs depicting the expression of EGFP and UCP2 in the presence of dsRNA.

FIG. 10 is a graph depicting the effect of dsRNA in differentiated N2a cells. Real-time PCR was used to measure the levels of 14-3-3 mRNA from cells transfected with lipofectamine alone, dsRNA 14-3-3, and dsRNA EGFP. Data presented were mean from two technical repeats. Similar results were obtained in two independent experiments.

DETAILED DESCRIPTION OF THE EMBODIMENTS

I. Definitions

Figure 1:
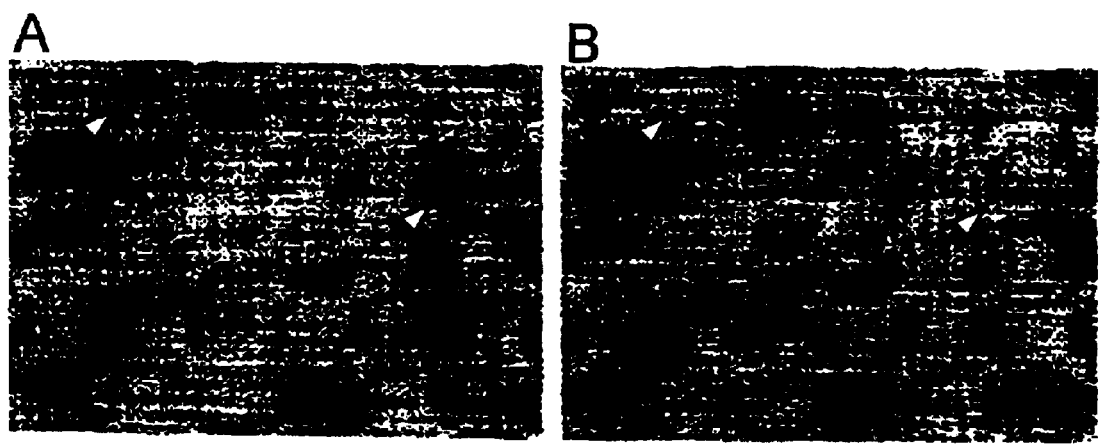
FIG. 1 shows duplicate arrays probed using the "knock-down" methods of the invention. Arrows show (A) presence of hybridization signal (triplicate spots) and (B) reduction of signal due to inclusion of knock-down polynucleotide during hybridization. This figure shows a portion (detail) of a larger array.

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

Various biochemical and molecular biology methods are well known in the art. For example, methods of isolation and purification of nucleic acids are described in detail in WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993); Chapter 3 of Laboratory Techniques in Biochemistry and Molecular Biology: Hybridization With Nucleic Acid Probes, Part 1. Theory and Nucleic Acid Preparation, (P. Tijssen, ed.) Elsevier, N.Y. (1993); and Sambrook et al., Molecular Cloning: A Laboratory Manual, Cold Spring Harbor Press, N.Y., (1989); and Current Protocols in Molecular Biology, (Ausubel, F. M. et al., eds.) John Wiley & Sons, Inc., New York (1987–1999), including supplements such as supplement 46 (April 1999).

As used herein, the following terms have the meanings ascribed to them unless specified otherwise:

The term "tissue," as used herein in the context of a source of mRNA and cDNA, refers to any aggregation of morphologically or functionally related cells, or cell systems, and thus includes cells (including in vitro cultured cells), tissues, organs, and the like.

The term "library" as used herein, refers to a collection of polynucleotides (usually in the form of double-stranded cDNA) derived from mRNA of a particular tissue. The polynucleotides of a library may be, but are not necessarily, cloned into a vector.

The terms "nucleic acid" "polynucleotide" and "oligonucleotide" are used interchangably herein and refer to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). A "subsequence" or "segment" refers to a sequence of nucleotides that comprise a part of a longer sequence of nucleotides.

A "gene," for the purposes of the present disclosure, includes a DNA region encoding a gene product (see infra). The region can also include DNA regions that regulate the production of the gene product, whether or not such regulatory sequences are adjacent to coding and/or transcribed sequences. Accordingly, a gene can include, without limitation, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" refers to a change in the level or magnitude of an activity or process. The change can be either an increase or a decrease. For example, modulation of gene expression includes both gene activation and gene repression. Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961–964 (1997)); changes in signal transduction, phosphorylation and dephosphorylation, receptor-ligand interactions, second messenger concentrations (e.g., cGMP, cAMP, IP3, and Ca2+), and cell growth.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14–25 nucleotides, preferably at least 65%, more preferably at least 70%, at least about 75%, and most preferably at least 90%. Preferably, one nucleic acid hybridizes specifically to the other nucleic acid. See M. Kanehisa, *Nucleic Acids Res.* 12:203 (1984).

The term "exogenous" when used with reference to a molecule (e.g., a nucleic acid) refers to a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. An exogenous molecule can be the same type of molecule as an endogenous molecule, e.g., protein or nucleic acid (i.e., an exogenous gene), providing it has a sequence that is different from an endogenous molecule. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, the term "endogenous" when used in reference to a molecule is one that is normally present in a particular cell at a particular developmental stage under particular environmental conditions.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids, refers to two or more sequences or subsequences that have at least 75%, preferably at least 80% or 85%, more preferably at least 90%, 95% or higher nucleotide identity, when compared and aligned for maximum correspondence, as measured using a sequence comparison algorithm such as those described below for example, or by visual inspection. Preferably, the substantial identity exists over a region of the sequences that is at least about 40–60 nucleotides in length, in other instances over a region at least 60–80 nucleotides in length, in still other instances at least 90–100 nucleotides in length, and in yet other instances the sequences are substantially identical over the full length of the sequences being compared, such as the coding region of a nucleotide for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987–1999, including supplements such as supplement 46 (April 1999)]. Use of these programs to conduct sequence comparisons are typically conducted using the default parameters specific for each program.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Natl. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to" or "specifically hybridizing to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe or primer will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. In other instances, stringent conditions are chosen to be about 20° C. or 25° C. below the melting temperature of the sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) Methods in Enzymology, vol. 152: Guide to Molecular Cloning Techniques, San Diego: Academic Press, Inc. and Sambrook et al. (1989) Molecular Cloning: A Laboratory Manual, 2nd ed., vols. 1–3, Cold Spring Harbor Laboratory), both incorporated herein by reference. As indicated by standard references, a simple estimate of the $T_m$ value can be calculated by the equation: $T_m=81.5+0.41(\% \text{ G}+\text{C})$, when a nucleic acid is in aqueous solution at 1 M NaCl (see e.g., Anderson and Young, "Quantitative Filter Hybridization," in Nucleic Acid Hybridization (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe or primer and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions can also be achieved with the addition of destabilizing agents such as formamide.

The term "detectably labeled" means that an agent (e.g., a probe) has been conjugated with a label that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

II. Overview

The present invention provides methods for efficiently identifying and characterizing genes that play important roles in cellular processes such as aging and development, response to environmental challenges (e.g., injury or drug exposure), and pathologic processes. Specifically, the methods disclosed herein permit the rapid and economical generation of "libraries" of differentially expressed and low abundance sequences likely to play roles in pathogenesis and treatment of human disease. Importantly, the methods of the invention are well suited to use with very small amounts of tissue. This permits comprehensive libraries to be produced even when small amount of starting material is available.

The methods also include a process in which genes identified as being present in low abundance and/or as being differentially expressed ("candidate genes") are functionally validated. This validation process involves determining whether a candidate gene does in fact play a functional effect in a cell by, for example, determining if modulation of expression of the candidate gene is correlated with an alteration in a cellular activity or cellular state in the cell in which expression is modulated.

Certain methods are performed using double-stranded RNA interference (RNAi). In general, such methods involve introducing a dsRNA that is specifically hybridizes to at least a segment of the candidate gene into a reference cell or tissue into which the dsRNA is introduced and then determining whether interference with expression is associated with alteration of cellular activity or state. Detection of such an alteration provides evidence that the candidate gene is correlated with the particular cellular state or process under investigation.

However, methods other than RNAi can be utilized to functionally validate candidate genes identified in the libraries. Such methods include interference with gene expression by use of antisense technology, ribozymes and gene knock-out approaches. Additional approaches include co-immunoprecipitation and epistasis investigations.

III. Preparation of Libraries

Generally

In one aspect of the invention, cDNA libraries are prepared that are highly enriched for gene sequences likely to play a role in the molecular and cellular mechanisms of disease, or which are involved in other important cellular processes. In one embodiment of the invention, four related, or "cognate," libraries are prepared and selected sequences analyzed. Although, in some embodiments of the invention, fewer than four libraries are prepared, by screening multiple (e.g., four) libraries the coverage of the transcriptome is maximized and the likelihood of identifying low-abundance and differentially-expressed genes is increased. Moreover, by preparing four libraries validation techniques, as described infra are facilitated.

Tissue Sources

The libraries of the invention are prepared using mRNA from pairs of tissues that are of the same type, but which differ in one major characteristic, such as disease state (e.g., diseased & normal brain tissue), age (e.g., adult and fetal liver tissue), exposure to drugs, state of differentiation, stage of development, or other state (e.g., stimulated & unstimulated; activated & unactivated). The tissue source may be human or non-human. Typically the tissues are from a mammal such as a human, non-human primate, rat, or mouse. In some embodiments, the tissues are from an animal or tissue culture model of a human disease, e.g., stroke, Alzheimer's disease, and neuropathy. Examples of tissue pairs useful for library preparation are shown in Table 1.

TABLE 1

| Gene-expression state 1 | Gene-expression state 2 |
| --- | --- |
| Diseased tissue | Normal tissue |
| a) hypoxic/ischemic brain | a) healthy brain |
| b) cirrhotic liver | b) healthy liver |
| c) tumor | c) normal tissue |
| d) Alzheimer's brain | d) healthy brain |
| Drug-exposed tissue | Non-drug exposed tissue |
| a) kainate-injected brain | a) saline injected brain |
| b) Zyprexa ®-injected brain | b) saline injected brain |
| c) toxin-stimulated cell line | c) saline stimulated cell line |
| Age/Tissue Type/etc. | Age/Tissue Type/etc. |
| a) mature brain | a) fetal brain |
| b) hippocampus | b) cortex |

TABLE 1-continued

| Gene-expression state 1 | Gene-expression state 2 |
| --- | --- |
| c) neurons | c) glial cells |

Although each of any group of four cognate libraries is prepared using the same tissue pair, the libraries have different properties as a result of differences in their construction. For each set of libraries, one tissue in the pair is designated the "driver tissue," "control tissue," or simply "control cell" (from which "driver" cDNA may be made) and the second tissue in the pair is designated the "tester" tissue, "test tissue," or simply "test cell" (from which "tester" cDNA may be made). For example, in a pair in the same horizontal row of Table I), the tissue in the first column may be considered the tester and the tissue in the second column may be considered the driver. For purposes of the invention, it is entirely arbitrary which tissue is "driver" and which is "tester."

For ease of reference, the four cognate libraries are referred to herein as: (1) driver-normalized, (2) tester-normalized, (3) driver-subtracted, and (4) tester-subtracted. Libraries (1) and (2) are normalized, and thus enriched in sequences corresponding to low abundance transcripts. In a cognate group, Library 1 is made using one tissue of a pair (driver tissue) and Library 2 is made using the specified tester tissue. Libraries (3) and (4) are subtracted (or normalized and subtracted) libraries and thus enriched in sequences that are differentially expressed between pairs of tissue states. Libraries (3) and (4) of a cognate group are made using both tissues in the tissue pair.

Several methods are known for making normalized and/or subtracted cDNA libraries. Although certain methods are described or referred to in Sections II(B)–(E), infra, the invention is not limited to embodiments in which these methods are used. For example, the analytical methods described in Section III may be used in combination with a variety of normalization/subtraction approaches.

Preparation of Double-stranded cDNA from Paired Tissue Samples

Double-stranded cDNA (dscDNA) is prepared from tissues using standard protocols, i.e., by reverse transcription of messenger (poly A$^+$) RNA from a specified RNA source using a primer to produce single stranded cDNA. Methods for isolation of total or poly(A) RNA and for making cDNA libraries are well known in the art, and are described in detail in Ausubel and Sambrook (supra). In one embodiment, the library is made using oligo(dT) primers for first strand synthesis. The single-stranded cDNA is converted into double-stranded cDNA (dscDNA) using routine methods (see, e.g., Ausubel supra).

Restriction Enzyme Digestion

In some embodiments of the invention, the dscDNA from each tissue source is digested with one restriction enzyme or, in an alternative embodiment, the dscDNA from each tissue source is separately digested with two or more restriction enzymes, with different specificities, that cut at recognition sequences found frequently in the dscDNA. Often, two enzymes are used (and the discussion and examples below will refer to use of two enzymes). As noted, the digestion with each of the two or more enzymes is carried out separately (e.g., in separate reaction tubes). The digested fragments may be combined later for further processing.

The dual digestion steps allow for the efficient generation of libraries that are more comprehensive (e.g., containing more different species of expressed or differentially expressed species) than libraries made by other methods. The digestion is intended, in part, to generate fragments in a size range that allows efficient hybridization during the annealing steps of library construction. Only fragments of the target size range will efficiently anneal under the conditions used, and non-annealing molecules are excluded from amplification or cloning in some embodiments of the invention. A further advantage of the dual digestion steps is that by digesting with multiple (e.g., 2) enzymes with different specificities as taught herein, the resulting libraries are more comprehensive.

According to the invention, the restriction enzymes used are selected that will produce a calculated (or "predicted") average fragment size of between about 100 and about 500 basepairs, preferably about 300–500 basepairs (e.g., an average length of between 300 bases and 500 bases). In addition, the two or more different enzymes should produce fragments of similar lengths (e.g., so that each has a calculated average fragment size of within about 150 bases, more often about 100 bases, of the calculated average fragment size of the other). Because PCR is generally more efficient for shorter fragments, the use of fragments of similar length also ensures non-biased PCR amplification between fragments resulting from digestion with different enzymes at subsequent steps in library construction.

The calculated average fragment size produced by digestion of a particular sample with a particular enzyme can be determined in a variety of ways. In one embodiment, a database of mRNA/cDNA sequences corresponding to a selected class of mRNAs is used as a representative proxy for the entire population of mRNAs of that class. One database suitable for this analysis is GenBank (accessible at, e.g., http://www.ncbi.nlm.nih.gov/). Using this method, a set of mRNA sequences known to be expressed in a specified tissue (e.g., brain), organism (e.g., rat, human), or phylum (e.g., mammalia) are identified. Such identification can be easily accomplished because sequences in databases such as GenBank are annotated, so that an investigator can select sequences with particular properties. The frequency and distribution of particular restriction enzyme recognition sites in the selected population of sequences is then determined, e.g., by inspection, but most conveniently by using a computer program such as GCG (Genetics Computer Group Inc., Madison, Wis.) or Sequencher (Gene Codes Corp, Ann Arbor, Mich.). In addition, the distribution of restriction sites in the population can be determined using publicly available computer software, and enzymes that frequently cut at clustered sites identified; such enzymes are less desirable than those that recognize more evenly distributed sites.

Table II summarizes an experiment in which enzymes suitable for use with dscDNA prepared from rat mRNA were identified. To identify these enzymes, a collection of 489 full-length rat mRNA/cDNA sequences was collected from GenBank. The selected sequences from rat included a poly A-signal at 3' end as well as an entire protein coding sequence (ORF) and at least 100 base pairs of 5' UTR. The mRNAs sequences analyzed had an average mRNA length of 2257 bases (and an average coding sequence length 1509 bases and average 3' untranslated region of 604 bases). The restriction pattern predicted for digestion of this polynucleotide set was determined using the GCG program described supra.

Exemplary enzymes for digestion of mammalian sequences include Alu I, Cvi RI, Dpn I, Hae III, Rsa I, Cvi J1 and Tha 1. As is apparent from the table, most suitable enzymes recognize 4-base restriction sites and are blunt-cutters. As determined in the experiment summarized in Table II, preferred combinations of enzymes for construction of libraries from mammalian sequences are Dpn I and Rsa I, because they produce fragments of similar size in the desired size range.

TABLE II

| Enzyme | Recognition site | Rec. sites/ mRNA | Not cleaved | Average size |
| --- | --- | --- | --- | --- |
| Alu I | AGCT | 13.07 | 0 | 175 |
| Cvi JI | RGCY | 51.89 | 0 | 47 |
| Cvi RI | TGCA | 11.36 | 3 | 199 |
| Dpn I | GATC | 07.17 | 13 | 319 |
| Hae III | GGCC | 13.23 | 0 | 216 |
| Rsa I | GTAC | 05.21 | 24 | 424 |
| Tha I | CGCG | 02.70 | 171 | 1044 |

In alternative embodiments, the average fragment size can be determined empirically. For example, average fragment size can be determined by PCR amplification of large number (e.g., at least 500) of clones from a normalized or subtracted library with vector-specific primers, followed by size determination of inserts on agarose gels.

As noted above, each restriction digestion is carried out separately (i.e., in a separate reaction vessel). Table III provides a flowchart illustrating the production of restriction digested dscDNA from a tissue pair using restriction enzymes Dpn 1 and Rsa 1. Parenthetical numbers are used to refer to specific products (i.e., reagents) produced or used for library production.

TABLE III a) Dpn 1 digest (1)
(normal) tissue →
b) Rsa 1 digest (2)
a) Dpn 1 digest (3)
(diseased) tissue →
b) Rsa 1 digest (4)

In embodiments in which digestion is carried out with a single enzyme, any enzyme that would have been suitable as part of an enzyme pair may be used (e.g., Dpn 1 or Rsa 1).

Addition of Adaptors

According to the invention, the digested fragments (e.g., digests 1–4 in Table III) are divided into two aliquots and each aliquot is ligated to an adaptor oligonucleotide, i.e., the first aliquot is ligated to a first adaptor and the second aliquot is ligated to a second adaptor. The adaptors used are usually designed to create a 22 to 40 base upper strand hybridized to a 8–12 base lower strand (i.e., partially double-stranded). Adaptors are ligated to dscDNA fragments using methods well known in the art. For example, unphosphorylated oligonucleotides may be ligated to dscDNA fragments in a standard ligation reaction (e.g., a buffered mixture containing adaptors, fragments, 0.3 mM ATP and T4 DNA ligase, incubated for 12 h at 14° C.).

The adaptors are designed according to the following criteria: 1) The ligation of the adaptor to the fragment should reconstitute the restriction enzyme recognition sequence for the restriction enzyme used to produce the fragments; 2) The adaptor should have a sequence sufficiently long and complex to serve as targets for amplification by the polymerase chain reaction (PCR), e.g., nested PCR. 3) The first and second adaptors should have different sequences so that a molecule containing both adaptor sequences at opposite ends of a fragment can be differentiated from a molecule containing the same adaptor sequence at each end by PCR amplification using suitable primers.

Methods for preparation of normalized and subtracted libraries by using adaptors suited to PCR amplification are known in the art and may be referred to in the practice of the present invention. See, e.g., Straus and Ausubel, 1990, *Proc. Natl. Acad. Sci.* 87: 1889; and Diatchenko et al., 1996, *Proc. Natl. Acad. Sci.* 93:6025–30; see also U.S. Pat. No. 5,759,822, all of which are incorporated herein by reference.

Exemplary adaptors are shown in Table IV, along with primer sets that may be used for PCR amplification:

TABLE IV

| No | first adaptor | second adaptor | Corresponding primers |
|---|---|---|---|
| 1* | (SEQ ID NO:1) 5'-CTAATACGACT CACTATAGGGCTCG AGCGGCCGCCCGGG CAGGT-3' | (SEQ ID NO:2) 5'-CTAATACGACTCA CTATAGGGCAGCGTGG TCGCGGCCGAGGT-3' (SEQ ID NO:5) 5'-ACCTCGGCC G-3' | (SEQ ID NO:3) 5'-CTAATACGACT CACTATAGGGC-3'; (SEQ ID NO:6) Nested PCR Primer 1: 5'-TCGAGCG GCCGCCCGGGCA GGT-3' (SEQ ID NO:7) Nested PCR Primer 2: 5'-AGC GTGGTCGCGGCCGAGG T-3' |
| | (SEQ ID NO:4) 5'-ACCTGCCC GG-3' | | |
| 2* | (SEQ ID NO:8) 5'-TCGAGCGG CCGCCCGGGCAGG T-3' | (SEQ ID NO:10) 5'-AGCGTGGTCG CGGCCGAGGT-3' | (SEQ ID NO:12) 5'-TCGAGCGGCCGCC CGGGCAGGT-3' |
| | (SEQ ID NO:9) 5'-ACCTGCCCGG- 3' | (SEQ ID NO:11) 5'-ACCTCGGCCG-3' | (SEQ ID NO:13) 5'-AGCGTGGTCGC GGCCGAGGT-3' |

*partially double-stranded.

Table V provides, in schematic terms, a flowchart illustrating the addition of adaptors to the products of Table III. In the illustration, the first adaptor is designated "Adaptor A" or "Adaptor C," and the second adaptor is designated "Adaptor B" or "Adaptor D," with different first and second adaptors being used for fragments produced using different restriction enzymes. Although pairs such as A and C or B and D will have different sequences at the end ligated to the fragment (so that the appropriate restriction fragment is regenerated upon ligation), to the extent possible the adaptors are designed to share the same sequence, e.g., to facilitate subsequent PCR amplification.

TABLE V

| | | |
|---|---|---|
| (normal) tissue → | a) Dpn 1 digest (1) → | i) adaptor A (1A) |
| | | ii) adaptor B (1B) |
| | b) Rsa 1 digest (2) → | iii) adaptor C (2C) |
| | | iv) adaptor D (2D) |
| (diseased) tissue → | a) Dpn 1 digest (3) → | i) adaptor A (3A) |
| | | ii) adaptor B (3B) |
| | b) Rsa 1 digest (4) → | iii) adaptor C (4C) |
| | | iv) adaptor D (4D) |

The adaptor-ligated fragments corresponding to each of the separate digestion reactions can be, and typically are, combined before proceeding to the subsequent subtraction and normalization protocols. For example, referring to Table V, supra, 1A+2C, 1B+2D, 3A+4C, 3B+4D may be combined if adaptors A and C and adaptors B and D differ only at the 3' end (in order to reconstitute the restriction site). However, if desired, the reactions may be combined at later stages, or, alternatively, they may be kept separate.

Production of Subtracted Libraries

Subtracted libraries (i.e., normalized-subtracted libraries) are used to identify efficiently genes that are differentially expressed in a pair of tissues. Two subtracted libraries are produced, a "driver-subtracted" library and a "tester-subtracted library." When the "tester tissue" is stimulated tissue and the "driver tissue" is unstimulated, the "driver-subtracted" library will be enriched for genes down-regulated by stimulation and the "tester-subtracted" library will be enriched for genes up-regulated by stimulation.

Methods for normalization, substraction and simultaneous normalization and subtraction are known (see, e.g., Ausubel §§5.8–5.9 and discussion infra). In one embodiment, the normalized-subtracted libraries of the invention are made essentially according to Diatchenko et al. supra. In another embodiment, the production of the normalized-subtracted libraries includes the following steps:

First Annealing Step

The following mixtures of adaptor-free digested fragments and adaptor-linked fragments are prepared and annealing reactions carried out (Table VI). The adaptor-free fragments are added in excess over the adaptor-linked fragments, e.g., at an about 20:1, 10:1, or 5:1 ratio. Multiple ratios can be used.

TABLE VI

| driver-subtracted | tester-subtracted |
|---|---|
| Rxn 1) anneal 1A + 3 | Rxn 5) anneal 3A + 1 |
| Rxn 2) anneal 1B + 3 | Rxn 6) anneal 3B + 1 |
| Rxn 3) anneal 2C + 4 | Rxn 7) anneal 4C + 2 |
| Rxn 4) anneal 2D + 4 | Rxn 8) anneal 4D + 2 |

The mixture is heat-denatured and allowed to anneal, e.g., by heat-denaturation for 90 seconds at 99° C. followed by incubation at 68° C. to allow annealing in 1 M NaCl, 50 mM HEPES (pH 8.3) and 4 mM Cetyltrimethylammonium bromide. Annealing is allowed to proceed to multiple different Cot values by incubating samples or aliquots for varying times (e.g., 4–12 h for a first sample and 10–24 h for second sample). Hybridization to multiple Cot values results in a more completely normalized library and/or increases the likelihood of enrichment of all differentially regulated genes. It will be recognized that in the annealing step, abundant sequences represented in the adaptor-ligated population will become double-stranded most rapidly, so that, as to adaptor-ligated single-stranded molecules, the library becomes enriched for low-copy number molecules present in the adaptor-ligated population. When annealing to multiple Cots is carried out, the products can be combined prior to the second annealing step, infra, or, alternatively, can be maintained separately throughout the amplification and optional cloning steps.

Second Annealing Step

The reactions mixtures of Table VI, supra, are combined and allowed to undergo a second hybridization step with excess (e.g., an about 20:1, 10:1, or 5:1 excess) freshly denatured driver (i.e., adaptor-free fragments), as shown in Table VII.

TABLE VII driver-subtracted

TABLE VII-continued

| | |
|---|---|
| Rxn 9) | products of Rxns 1 + 2 + additional denatured fragment 3* |
| Rxn 10) tester-subtracted | products of Rxns 3 + 4 + additional denatured fragment 4 |
| Rxn 11) | products of Rxns 5 + 6 + additional denatured fragment 1 |
| Rxn 12) | products of Rxns 7 + 8 + additional denatured fragment 2 |

*(see Tables III and VI)

Annealing is allowed to proceed to different Cot values by incubating samples or aliquots for various times (e.g. 4–20 h).

Amplification

After hybridization, PCR amplification is performed to isolate sequences of interest. In general, only molecules carrying adaptors at both ends can be amplified exponentially by PCR. Other species carry one adaptor at one end and are amplified with linear kinetics, whereas non-adaptor-ligated molecules are not amplified at all. Thus, the double adaptor-ligated population enriched in low-abundance or differentially expressed genes is isolated by PCR amplification. Typically, PCR amplification is done in a 2-step protocol using nested primers for the second amplification.

Production of Normalized Libraries

Normalization is the process by which redundant clones in a library are removed, without reducing the complexity of the library. After successful normalization, approximately equal numbers of all expressed genes are present in a library.

Typically normalization methods are based on reassociation kinetics of re-annealing of nucleic acids in which denatured DNA is hybridized to an excess amount of denatured complementary DNA. Because re-annealing nucleic acids follow approximately second-order kinetics, the most abundant species form double-stranded hybrids most quickly. Thus, at any given Cot, rare or less abundant species will preferentially remain single stranded and abundant species will enter the population of double-stranded molecules. Several methods are available for distinguishing, separating, or differentially amplifying the single stranded species. Exemplary normalization methods are found Soares et al., 1994, Proc Natl. Acad. Sci. 91:9228–32; Bonaldo et al., 1996, Genome Res. 6:791–806; and U.S. Pat. Nos. 5,637,685; 5,846,721; 5,482,845; 5,830,662; 5,702,898; and Ausubel, supra.

In one embodiment, two normalized libraries (referred to as "tester-normalized and "driver-normalized") are produced. In one embodiment, each normalized library is produced essentially according to the protocol described in §F, supra, except that the driver and tester are identical. Thus, in one embodiment, the following reactions in Table VIII are carried out.

TABLE VIII

| driver-normalized | tester-normalized |
|---|---|
| Rxn 1) anneal 1A + 1 | Rxn 5) anneal 3A + 3 |
| Rxn 2) anneal 1B + 1 | Rxn 6) anneal 3B + 3 |
| Rxn 3) anneal 2C + 2 | Rxn 7) anneal 4C + 4 |
| Rxn 4) anneal 2D + 2 | Rxn 8) anneal 4D + 4 |

It will be appreciated that, if desired, reactions 1 and 2, 3 and 4, 5 and 6, and 7 and 8 can be combined.

IV. Optimized Selection of Species for Further Analysis

For each library produced, further analysis is carried out to identify sequences likely to be of particular interest. These include genes in the low abundance classes from normalized libraries and differentially expressed genes.

The combination of screening both normalized as well as normalized-subtracted libraries allows comprehensive analysis of the actual expression status of the material under investigation. Previous methods for gene expression analysis operating on a large set of genes (cDNA arrays, oligonucleotide arrays), require the a priori knowledge of the genes under investigation and are considered to be "closed" systems. In contrast, the method disclosed herein combines high-throughput methods for identification of rare or differentially expressed genes, but also permits analysis with no prior knowledge about the gene expression changes expected. That is, the genes under investigation are generated by the method itself and are usually significantly more relevant for the biological process than a preselected set of genes.

Generally

In one embodiment, the preferentially amplified or cloned products of subtraction, normalization or combination subtraction-normalization methods are obtained, as described above or by other methods of normalization and/or subtraction. The resulting cDNA (libraries) are subcloned by ligation into a vector capable of propagation in a bacterial or eukaryotic cell. Typically, the clones are propagated in bacterial cells. A number of suitable vectors and cloning methods are known (see, e.g., Sambrook, and Ausubel, both supra), including "TA" cloning of PCR products (Stratagene, La Jolla, Calif.) or blunt-end ligation into a vector of fragments following a fill-in reaction using T4 DNA polymerase and dNTPs.

Further analysis is then carried out by propagating a large number of clones (i.e., by growing a large number of colonies or plaques containing clones from the library(s)). Typically, at least about 5000 clones, more often 10,000, sometimes 15,000 and frequently 25,000 clones are propagated. Because of the large number of clones that are analyzed, it is most convenient and practical to grow clones in multiwell plates (e.g., 384-well plates), using robotic means for growing and picking colonies. Suitable means are known in the art and are described at, e.g., Nguyen et al., 1995, Genomics 29:207–216. Alternatively, large numbers of clones can be grown and picked manually.

The insert (i.e., cloned sequences) from each of the clones is isolated and positioned on an array for further analysis. That is, the insert DNAs are immobilized at identified positions in a matrix suitable for hybridization analysis. In one embodiment, high-density filter arrays (HDFA) containing up to 12,000 PCR products per 8×12 cm membrane are used (Nguyen et al, supra). Alternatively, sequences may "printed" onto glass plates, as is described generally by Schena et al., 1995, Science 270:467–470.

Most conveniently, the insert corresponding to each clone is amplified by PCR using vector specific primers for spotting on the array. However, other approaches can be used. For example, DNA from each clone can be isolated, the DNA can be digested with a restriction enzyme(s) that cuts at the boundary of the vector and insert, and the insert sequence can be isolated and spotted on the array.

The arrayed sequences are then probed with labeled cDNA derived from "driver" (e.g., unstimulated) tissue or "tester" (e.g., stimulated) tissue. Labeled probes can be prepared using methods known in the art, e.g., by reverse transcription of isolated RNA from the driver and tester tissues in the presence of radiolabeled or fluorescently-labeled nucleotides (see, e.g., Ausubel, supra; Kricka, 1992, Nonisotopic DNA Probe Techniques, Academic Press San Diego, Calif.; Zhao et al., 1995, Gene 156:207; Pietu et al., 1996 Genome Res. 6:492). Alternative methods for preparing probes, e.g., riboprobes, are well known and their use is contemplated in some embodiments of the invention.

Optimal hybridization conditions for probing will depend on the type of array (e.g., filter, slide, etc.) selected, the method of labeling probe, and other factors. Hybridization is carried out under conditions of excess immobilized (arrayed) nucleic acid. General parameters for specific (i.e., stringent) hybridization conditions for nucleic acids are described in Sambrook and Ausubel. Suitable hybridization conditions for probing high density arrays are provided in Shena et al., 1996, *Proc. Natl. Acad. Sci. USA*, 93:10614, and Nguyen, supra.

When fluorescently labeled probes are used, the fluorescence emissions at each site of a transcript array are detected (e.g., by scanning confocal laser microscopy or laser illumination, see, e.g., Shalon et al., 1996, *Genome Research* 6:639–645; Schena et al., 1996, *Genome Res.* 6:639–645; Ferguson et al., 1996, *Nature Biotech.* 14:1681–1684). When radiolabeled probes are used, autoradiography or quantitative imaging systems (e.g., FUJIX BAS 1000 (Fugi)) may be used. See Nguyen et al., supra, and references cited therein. When it is desirable to determine the ratio of hybridization of two or more probes to the same set of clones, multiple copies of a specific array can be prepared, separately probed, the hybridization intensity be determined for each clone, and a ratio determined. Alternatively, a single array can be repeatedly probed, with washing steps between hybridizations. When differently labeled (e.g., fluorescently-labeled) probes are used, multiple (e.g., 2) differently labeled probes may be simultaneously hybridized to the same matrix (e.g., rhodamine-labeled driver cDNA and fluorescein-labeled driver cDNA), and, for any particular hybridization site on the transcript array, a ratio of the emission of the two fluorophores can be calculated from simultaneous hybridization to the same array.

One goal of the hybridization is to identify clones corresponding to mRNAs expressed at low abundance in driver and tester tissues, particularly clones corresponding to differentially expressed sequences. In the case of normalized libraries, both driver-normalized and tester-normalized libraries are probed with labeled cDNA from the tissue from which they are derived, as indicated in Table IX. Because the signal intensity for any arrayed clone will correspond to the abundance of the corresponding mRNA in the tissue, clones with low intensity signals (i.e., "low signal clones") will correspond to low abundance transcripts (i.e., mRNAs rare in the transcriptome). A "low intensity signal" or "low signal clone" refers to a clone having a hybridization signal in the lowest (e.g., $1^{st}$ to $20^{th}$ percentile) or very lowest (e.g., $1^{st}$ to $5^{th}$ percentile) range in a ranking of a large number (e.g., 1000) of clone signals in the array. This mRNA class is believed to be enriched for sequences of pharmaceutical importance.

TABLE IX

| Array | Probe | Selection |
|---|---|---|
| driver-normalized library array | labeled cDNA probe from driver tissue (e.g., stimulated tissue) | select low signal clones |
| tester-normalized library array | labeled cDNA probe from tester tissue (e.g., unstimulated tissue) | select low signal clones |

There are several advantages to screening both the tester- and driver-normalized libraries. Disease, drug exposure, and other stimulation leads to changes in the overall composition of the transcriptome as well as to transitions of genes from one abundance class into another. Thus, the identity of the expressed genes as well as their expression levels will be different for the two tissues. These differences will be reflected in the composition of the two libraries both because normalization is never complete (i.e., the resulting library is never perfectly normalized) and, second, because low abundance genes from one library are sometimes not found in the other.

In the case of the subtracted libraries (i.e., the driver-subtracted and tester-subtracted libraries), both are probed using labeled probes (e.g., cDNA probes) from both RNA sources (i.e. cDNA from driver tissues and cDNA from tester tissues). The ratio between the signals obtained by tester and driver probes indicates the up-regulation or down-regulation of a given clone in response to a stimulus. Thus, probing both driver-subtracted and tester-subtracted libraries will identify all genes that change in expression, either by up-regulation (tester-subtracted) or down-regulation (driver-subtracted). Typically, genes showing at least a 20% (1.2-fold) change are of interest, with genes showing a 2-fold difference in expression considered to be of particular interest. Preferably, the genes show at least about a 3-fold, 5-fold or 10-fold difference in expression. Clones exhibiting these differences in expression, as detected by hybridization of different probes, are referred to as "high ratio" clones.

TABLE X

| Array | Probe | Selection |
|---|---|---|
| driver-subtracted (e.g., enriched for sequences down-regulated in stimulated tissue) | A. labeled cDNA probe from driver tissue B. labeled cDNA probe from tester tissue | Select a high ratio of A:B Optionally select clones where either A or B give a low intensity signal |
| tester-subtracted (e.g., enriched for sequences up-regulated in stimulated tissue) | A. labeled cDNA probe from driver tissue B. labeled cDNA probe from tester tissue | Select a high ratio of B:A Optionally select clones where either A or B give a low intensity signal |

The hybridization analysis described provides an efficient way for prioritizing clones of likely high pharmaceutical significance for further analysis. Selected clones are usually characterized by DNA sequencing and homology analysis. Genes derived from such normalized libraries are used as a representative, relevant and non-redundant gene collection of a particular tissue and a particular biological question for a variety of downstream applications. These genes can serve as targets for array analysis allowing one to quantitate gene expression changes in the same or other biological models and complement the gene collection identified by normalized-subtracted libraries. The analysis of a number of normalized libraries from a variety of central and peripheral tissues under different conditions of stimulation provides an avenue for the ultimate identification of all genes expressed in the species under investigation. In addition, it will be appreciated that, in some embodiments, the arrayed sequences are screened with other probes; for example, an array of sequences differentially expressed in stroke vs. normal brain can be screened with cDNA probe made from mRNA of Alzheimer's Disease brain tissue.

"Knock-Down" Analysis

One advantage of the present method is that, among the genes selected for further analysis on the basis of hybridization, the level of redundancy is low (i.e., the number genes that are repeatedly sequenced is low) and the percentage of novel genes detected (genes not previously reported in GenBank) is high.

In contrast, some prior art DNA libraries contain clones representing a small number of parent genes comprise a large proportion of all the clones in the library. These highly represented (or highly redundant) genes are particularly common in non-normalized libraries, or in libraries from less complex sources, such as specific sub-regions of tissue or cell lines. Random selection of genes from such a library for analysis (e.g. sequencing) results in significant redundancy of effort and expense.

The "knock-down" methods of the invention can be used to further reduce redundancy both in the libraries described herein supra, and in libraries prepared by altogether other means (including non-normalized libraries or libraries prepared from specific sub-regions of tissue or cell lines). The knock-down method is used to identify clones that are redundant in a library (i.e., clones generated from transcripts having the same sequence) so that the effort and expense of characterizing the redundant sequences is avoided.

According to the knock-down method, redundant sequences in the library are identified by "prior sampling." That is, prior to the hybridization analysis described in Section III(A), supra, or the equivalent of such hybridization, the DNA sequence is determined for representative number of clones, usually at least 50, often between about 100 to about 400 clones, and sometimes more, for example, about 1000 clones. These analyzed clones are referred to as the "prior sample." It is not necessary to sequence the entire clone; rather only one, or optionally both, termini need be sequenced (e.g., typically at least about 50 bases are determined, more often between about 200 and 350 bases). The sequences are analyzed, for example by BLAST searching (Altschul et al., 1990, *J Mol. Biol.* 5:403–10). A redundant sequence will appear more often than average: For example, a BLAST-identified sequence appearing as more than 4% of the sample is considered redundant.

In one embodiment of the invention, a set of previously identified genes are included as "knock-down" (e.g., unlabeled) polynucleotide in the "knock-down" method, to identify and avoid further processing of clones that have already been characterized (e.g., sequenced).

If a particular clone or clones is found to be overrepresented when compared to other members of the library, DNA may be isolated from the clone(s) (e.g., by PCR amplification of the fragment or insert) and included as an unlabeled (e.g., blocking), or distinctly labeled polynucleotide, during a hybridization of a labeled probe mixture against an array of clones from the library, as described in Section III(A) supra. Typically the unlabeled or distinctly labeled "knock-down" polynucleotide is included at a concentration of about 5 to about 100 ng/ml in the hybridization mixture, often from about 5 to about 40 ng/ml. Other useful concentrations will be apparent to one of ordinary skill following the guidance of this disclosure. The unlabeled or distinctly labeled polynucleotides are referred to herein as "knock-down" polynucleotides. In one embodiment, a small number of redundant genes (e.g., one to ten) appearing in the "prior sample" may be included as "knock-down" polynucleotides. In another embodiment, many or all genes appearing in the "prior sample" can be included as "knock-down" polynucleotides.

The included unlabeled (or distinctly labeled) "knock-down" polynucleotide will hybridize to complementary sequences in the labeled probe mixture, reducing the amount of specific labeled probe species available for hybridization to the array. Comparison of the signal of the probe with and without the addition of knockdown polynucleotide will show that the inclusion of the knock-down clone(s) reduces hybridization signals at particular sites on the matrix. The sites of reduced signal correspond to sequences that are represented in the set of "knock-down" polynucleotides (i.e., redundant sequences by frequency or known sequences by prior sampling). Having identified such clones, a decision may be made not to further analyze (e.g., sequence) the clones, saving time and effort.

Alternatively, when the "knock-down" polynucleotides are detectably labeled (using a label that can be distinguished from the probe label), redundant clones will be identifiable by the presence of the distinct signal at the matrix site. This requires an additional labeling step for the "knock-down" polynucleotides and, in one embodiment, requires an additional duplicate hybridization matrix or a measurement of the distinct signal. This is similar to the effort of measuring the signal of the primary (non-knock-down) labeled probe with and without the inclusion of "knock-down" polynucleotides.

Alternately, redundant clones are identified by hybridization of single clones against an array representing the library, rather than by sequence analysis as discussed supra. A redundant clone will appear more than once, and more highly redundant clones will tend to appear more than less redundant clones. Non-redundant clones will appear once. In this embodiment, duplications of the array allow testing of as many individual clones as desired to test their redundancy, and the decision may be made to not further analyze (e.g., sequence) the clones, saving time and effort.

V. Analysis of Methods of Library Construction cDNA libraries are a critical reagent used by biologists in the analysis of gene expression and function. Various methods have been used to produce normalized and/or subtracted cDNA libraries (see, e.g., §II supra and Ausubel, supra). These methods are complex and entail numerous different parameters (e.g., annealing times, polynucleotide concentrations, primer choices, amplification conditions, and the like), all of which may affect library quality in sometimes unpredictable ways. However, the art lacks a convenient and economical method for evaluating the quality of normalized and/or subtracted cDNA libraries.

As used herein, the "quality" of a subtracted (or normalized-subtracted) library is assessed by the degree to which differentially expressed genes are enriched in the library relative to non-differentially expressed genes. As used herein, the "quality" of a normalized-library (e.g., a tester-normalized or driver-normalized library) is assessed by the degree to which sequences in the library are present in the same abundance.

The present invention provides methods for conveniently assessing library quality. By comparing the quality of libraries made using starting RNA from the same source but made by using different methods, the superior method can be identified (by virtue of producing a higher quality library).

In one embodiment, the method involves making libraries from the same tester and driver RNA but varying parameters. Detectably labeled probe is made from DNA from each library, using standard methods (e.g., nick translation, Ausubel, supra). The resulting probes are hybridized to an array of immobilized polynucleotides under conditions of specific hybridization.

Suitable polynucleotide arrays may be produced by any of a variety of methods, but typically are spotted onto glass slides or nylon membranes (e.g., Schena et al., 1995, *Science* 270:467–470, and Zhao et al., 1995, *Gene* 156:207–213). The array is selected to contain at least some polynucleotide sequences representing genes that are differentially expressed in the tester RNA tissue compared to the driver RNA tissue. This may be accomplished generally in two different ways.

In one method, a reference library (e.g. a tester-subtracted library) is produced from tester and driver RNA (e.g., as described supra). Typically, the tester and driver RNA used for preparation of the reference library is made from the same tissue sources as used for the libraries to be assessed, although it will be appreciated that this is not strictly necessary. The resulting library is cloned (e.g., by ligation to a vector and transform of bacteria) and DNA corresponding to individual clones prepared (e.g., by PCR amplification using vector primers). DNA from a plurality of the clones (typically at least 50, more often at least 100, more often at least 1000) is applied to a substrate (e.g., glass slide) for hybridization as described infra. The resulting cDNAs are spotted onto substrate (e.g. nylon or glass) and the substrate is treated to affix the cDNAs. The array will include differentially expressed sequences (reflecting the library from which the clones were prepared).

A second method for selection of genes can rely on publications for selection of genes previously reported to be expressed in the tester RNA at higher levels than the driver RNA. These can be identified by their Genbank identifier number, and many can be ordered from commercial sources, and these can be amplified by gene specific primers with PCR.

The resulting arrays are then prehybridized, and hybridized with probe described supra. After hybridization (including appropriate washing), the degree of hybridization of each library to various immobilized polynucleotides is detected and compared (e.g., the detectable signal is quantitated). As shown in the Examples, and in FIGS. 2–4, the intensity of hybridization of the labeled probe to an immobilized polynucleotide in the array is indicative of the relative abundance of the probe sequence in the library. For example, the more enriched a library is for a differentially expressed gene, the greater the intensity of the hybridization of probe from that library to the immobilized gene sequence.

According to the invention, a higher quality library is identified because at least one differentially expressed sequence shows higher hybridization signal (compared to a library of lower quality). More often, a higher quality library is characterized by a higher hybridization signal to a plurality of different differentially expressed genes on the array, e.g., at least about 5, 10, 20 or 30 sequences or at least about 5%, 10% or 50% of the genes on the array that are differentially expressed (i.e., show an at least 1.2-fold, preferably an at least 2-fold, often at least 3-fold difference in expression between the tester and driver RNAs). If the differentially expressed sequence is rare (i.e. expressed at a low level relative to the average sequence expression level), the hybridization signal of the rare sequence in the improved subtracted-normalized library will increase relative to a tester-subtracted library. Conversely, if a differentially expressed sequence is abundant (i.e. expressed at a higher level relative to the average sequence expression level), the hybridization signal of the abundant sequence in the improved subtracted-normalized library will decrease relative to a tester-subtracted library. Thus, the method provides for the detection of rare clones that are differentially expressed between two conditions.

VI. Functional Analysis of Identified Genes

Once a gene has been identified as potentially correlated with a particular cellular state or activity, the gene can be subjected to a functional validation process to determine from a functional standpoint whether the gene plays a role in a particular cellular activity or establishment of a cellular state. Such genes are referred to herein as "candidate genes." Candidate genes can potentially be correlated with a wide variety of cellular states or activities. Examples of such states and activities include, but are not limited to, states related to exposure to certain stimuli (e.g., drugs, toxins, environmental stimuli), disease, age, cellular differentiation and/or stage of development.

In general, the term "functional validation" as used herein refers to a process whereby one determines whether modulation of expression of a candidate gene or set of such genes causes a detectable change in a cellular activity or cellular state for a reference cell, which cell can be a population of cells such as a tissue or an entire organism. The detectable change or alteration that is detected can be any activity carried out by the reference cell. Specific examples of activities or states in which alterations can be detected include, but are not limited to, phenotypic changes (e.g., cell morphology, cell proliferation, cell viability and cell death); cells acquiring resistance to a prior sensitivity or acquiring a sensitivity which previously did not exist; protein/protein interactions; cell movement; intracellular or intercellular signaling; cell/cell interactions; cell activation (e.g., T cell activation, B cell activation, mast cell degranulation); release of cellular components (e.g., hormones, chemokines and the like); and metabolic or catabolic reactions.

In one particular embodiment, candidate genes generally correspond to genes expressed at low levels and/or genes that are differentially expressed with respect to different cells (e.g., diseased cells versus healthy cells). Low level candidate genes are those whose mRNA is about 20% or less of the total mRNA within a cell or a library prepared therefrom. Preferably about 15% or less, more preferably about 10% or less, still more preferably about 5% or less, yet still more preferably about 1% or lesss, and most preferably about 0.1% or less. In some instances, the low abundance genes are 1% or less of the total mRNA in the cell or library prepared therefrom. Genes that are differentially expressed are genes in which there is a detectable difference in expression between the different cells/tissues being compared. Generally, this means that there is at least a 20% change, and in other instances at least a 2-, 3-, 5- or 10-fold difference. The difference usually is one that is statistically significant, meaning that the probability of the difference occurring by chance (the P-value) is less than some predetermined level (e.g., 0.05). Usually the confidence level P is <0.05, more typically <0.01, and in other instances, <0.001. Both low abundance genes and differentially expressed genes can be identified, for example, according to the methods disclosed supra in section IV.

A variety of options are available for functionally validating candidate genes identified according to the foregoing methods. One particular aspect of the present invention provides a high-throughput functional validation, which generally involves using the transcriptome procedure described herein. In this manner, once the expression of a gene is determined to correlate with a particular cellular state and/or cellular activity, at least a partial clone of the gene is already available from the transcriptome in the form of plasmid containing T7/T3 promoter. Alternatively, a promoter can be added to such partial clone of the gene, e.g., using PCR approach.

Double-stranded RNA Interference (RNAi)

As described in the following sections and in further detail in Examples 4 and 5 infra, the current inventors have demonstrated that RNAi technology is an effective approach for functionally validating candidate genes identified through the foregoing gene identification methods. As used herein, RNAi technology refers to a process in which double-stranded RNA is introduced into cells expressing a candidate gene to inhibit expression of the candidate gene, i.e., to "silence" its expression. The dsRNA is selected to have substantial identity with the candidate gene.

The mechanism by which dsRNA exerts its inhibitory effect is not fully understood. However, researchers in the RNAi field currently believe that dsRNA suppresses the expression of endogenous genes by a post-transcriptional mechanism. Specificity in inhibition is important because accumulation of dsRNA in mammalian cells can result in the global blocking of protein synthesis. This blockage appears to result because even low doses of dsRNA (such as occasioned by viral infection, for example) can induce what is called the interferon response. It is believed that in some cases, this response leads to the activation of a dsRNA-responsive protein kinase simply referred to as PKR. Following activation, PKR phosphorylates and inactivates EIF2α, thereby causing global suppression of translation, which in turn triggers cellular apoptosis. However, the present inventors have found that when AGYNB-010 cells are used, there is a minor upregulation of IFN-β, with no significant global suppression of translation, which in turn results in no apoptosis.

The gene identification procedures set forth herein when coupled with RNAi technology enables high throughput analysis and validation of a large number of genes for any particular cellular state or activity of interest. In general such methods initially involve transcribing a nucleic acids containing all or part of a candidate gene into single- or double-stranded RNA. Sense and anti-sense RNA strands are allowed to anneal under appropriate conditions to form dsRNA. The resulting dsRNA is introduced into reference cells via various methods and the degree of attenuation in expression of the candidate gene is measured using various techniques. Usually one detects whether inhibition alters a cellular state or cellular activity.

Nature of the dsRNA

The dsRNA is prepared to be substantially identical to at least a segment of a candidate gene. In general, the dsRNA is selected to have at least 70%, 75%, 80%, 85% or 90% sequence identity with the candidate gene over at least a segment of the candidate gene. In other instances, the sequence identity is even higher, such as 95%, 97% or 99%, and in still other instances, there is 100% sequence identity with the candidate gene over at least a segment of the candidate gene. The size of the segment over which there is sequence identity can vary depending upon the size of the candidate gene. In general, however, there is substantial sequence identity over at least 15, 20, 25, 30, 35, 40 or 50 nucleotides. In other instances, there is substantial sequence identity over at least 100, 200, 300, 400, 500 or 1000 nucleotides; in still other instances, there is substantial sequence identity over the entire length of the candidate gene, i.e., the coding and non-coding region of the candidate gene. Suitable regions of the gene include the 5' untranslated region, the 3' untranslated region, and the coding sequence.

Because only sequence similarity between the candidate gene and the dsRNA is necessary, sequence variations between these two species arising from genetic mutations, evolutionary divergence and polymorphisms can be tolerated. Moreover, as described further infra, the dsRNA can include various modified or nucleotide analogs.

Usually the dsRNA consists of two separate complementary RNA strands. However, in some instances, the dsRNA may be formed by a single strand of RNA that is self-complementary, such that the strand loops back upon itself to form a hairpin loop. Regardless of form, RNA duplex formation can occur inside or outside of a cell.

The size of the dsRNA that is utilized varies according to the size of the candidate gene whose expression is to be suppressed and is sufficiently long to be effective in reducing expression of the candidate gene in a cell. Generally, the dsRNA is at least 10–15 nucleotides long. In certain applications, the dsRNA is less than 20, 21, 22, 23, 24 or 25 nucleotides in length. In other instances, the dsRNA is at least 50, 100, 150 or 200 nucleotides in length. The dsRNA can be longer still in certain other applications, such as at least 300, 400, 500 or 600 nucleotides. Typically, the dsRNA is not longer than 3000 nucleotides. The optimal size for any particular candidate gene can be determined by one of ordinary skill in the art without undue experimentation by varying the size of the dsRNA in a systematic fashion and determining whether the size selected is effective in interfering with expression of the candidate gene.

Synthesis of dsRNA dsRNA can be prepared according to any of a number of methods that are known in the art, including in vitro and in vivo methods, as well as by synthetic chemistry approaches.

In vitro methods. Certain methods generally involve inserting the segment corresponding to the candidate gene that is to be transcribed between a promoter or pair of promoters that are oriented to drive transcription of the inserted segment and then utilizing an appropriate RNA polymerase to carry out transcription. One such arrangement involves positioning a DNA fragment corresponding to the candidate gene or segment thereof into a vector such that it is flanked by two opposable polymerase-specific promoters that can be same or different. Transcription from such promoters produces two complementary RNA strands that can subsequently anneal to form the desired dsRNA. Exemplary plasmids for use in such systems include the plasmid (PCR 4.0 TOPO) (available from Invitrogen). Another example is the vector pGEM-T (Promega, Madison, Wis.) in which the oppositely oriented promoters are T7 and SP6; the T3 promoter can also be utilized.

In a second arrangement, DNA fragments corresponding to the segment of the candidate gene that is to be transcribed is inserted both in the sense and antisense orientation downstream of a single promoter. In this system, the sense and antisense fragments are cotranscribed to generate a single RNA strand that is self-complementary and thus can form dsRNA.

Various other in vitro methods have been described. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety.

Single-stranded RNA can also be produced using a combination of enzymatic and organic synthesis or by total organic synthesis. The use of synthetic chemical methods enable one to introduce desired modified nucleotides or nucleotide analogs into the dsRNA.

In vivo methods. dsRNA can also be prepared in vivo according to a number of established methods (see, e.g., Sambrook, et al. (1989) Molecular Cloning: A Laboratory Manual, $2^{nd}$ ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

Annealing Single-stranded RNA.

Once the single-stranded RNA has been formed, the complementary strands are allowed to anneal to form duplex RNA. Transcripts are typically treated with DNAase and further purified according to established protocols to remove proteins. Usually such purification methods are not conducted with phenol:chloroform. The resulting purified transcripts are subsequently dissolved in RNAase free water or a buffer of suitable composition.

dsRNA is generated by annealing the sense and anti-sense RNA in vitro. Generally, the strands are initially denatured to keep the strands separate and to avoid self-annealing. During the annealing process, typically certain ratios of the sense and antisense strands are combined to facilitate the annealing process. In some instances, a molar ratio of sense to antisense strands of 3:7 is used; in other instances, a ratio of 4:6 is utilized; and in still other instances, the ratio is 1:1.

The buffer composition utilized during the annealing process can in some instances affect the efficacy of the annealing process and subsequent transfection procedure. While some have indicated that the buffered solution used to carry out the annealing process should include a potassium salt such as potassium chloride (at a concentration of about 80 mM), the current inventors have found that the use of buffered solutions that are substantially potassium free can provide improved results. As used herein the term "substantially potassium free" means that a potassium salt is not added to the buffer solution; as a consequence, the potassium level is generally less than 1 $\mu$M, and more typically less than 1 nM. In one aspect of the present invention, it has been found by the current inventors that improved results can be obtained in some instances by using sodium chloride rather than potassium chloride in the annealing buffer solution. The sodium chloride concentration in the annealing buffer solution generally is at least 10 mM, and generally in the range 20 mM to 50 mM. Surprisingly and unexpectedly, present inventors have also found that further improved results can be obtained using sodium chloride free (i.e., <1 nM of sodium chloride) ammonium acetate at a concentration range of from about 10 $\mu$M to about 50 mM.

For example, certain annealing reactions are conducted in a solution containing 20 mM NaCl at 65° C. for 30 minutes, followed by cooling for 15 minutes. Alternatively, the annealing solution contains 10 mM TRIS (pH 7.5) and 20 mM NaCl at 95° C. for 1 minute and then allowing the solution to cool at room temperature overnight.

Once single-stranded RNA has annealed to form duplex RNA, typically any single-strand overhangs are removed using an enzyme that specifically cleaves such overhangs (e.g., RNAase A or RNAase T).

Introduction of dsRNA

Cells. Once the dsRNA has been formed, it is introduced into a reference cell, which can include an individual cell or a population of cells (e.g., a tissue, an embryo and an entire organism). The cell can be from essentially any source, including animal, plant, viral, bacterial, fungal and other sources. If a tissue, the tissue can include dividing or nondividing and differentiated or undifferentiated cells. Further, the tissue can include germ line cells and somatic cells. Examples of differentiated cells that can be utilized include, but are not limited to, neurons, glial cells, blood cells, megakaryocytes, lymphocytes, macrophages, neutirophils, eosinophils, basophils, mast cells, leukocytes, granulocytes, keratinocytes, adipocytes, osteoblasts, osteoclasts, hepatocytes, cells of the endocrine or exocrine glands, fibroblasts, myocytes, cardiomyocytes, and endothelial cells. The cell can be an individual cell of an embryo, and can be a blastocyte or an oocyte.

Certain methods are conducted using model systems for particular cellular states (e.g., a disease). For instance, certain methods provided herein are conducted with a neuroblastoma cell line that serves as a model system for investigating genes that are correlated with various neurological diseases. Examples of diseases that can be studied with this particular cell line include, but are not limited to, Alzheimer's disease, Parkinson's disease, brain tumor, epilepsy, stroke, especially ischemic stroke, and other neuro degenerative diseases.

One specific cell line is referred to by the present inventors as the AGYNB-010 cell line. This cell line is prepared as follows. Neuronal cells (ATCC CCL131) are passaged at least 30 times on media containing 0.10 mg/L of $Fe(NO_3)_3$ and 4500 mg/L of glucose. Cells so prepared have been found to be sensitivity to oxygen-glucose deprivation (OGD), N-methyl-D-aspartate (NMDA) and $\beta$-amyloid. As such, this particular line of cells serves as a useful model system for studying stroke (e.g., ischemic stroke), Alzheimer's disease and other neurological disorders. Other cell lines can be utilized as model systems to study obesity and brain tumor.

Delivery Options

A number of options can be utilized to deliver the dsRNA into a cell or population of cells such as in a cell culture, tissue or embryo. For instance, RNA can be directly introduced intracellularly. Various physical methods are generally utilized in such instances, such as administration by microinjection (see, e.g., Zernicka-Goetz, et al. (1997) Development 124:1133–1137; and Wianny, et al. (1998) Chromosoma 107: 430–439).

Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

If the dsRNA is to be introduced into an organism or tissue, gene gun technology is an option that can be employed. This generally involves immobilizing the dsRNA on a gold particle which is subsequently fired into the desired tissue. Research has also shown that mammalian cells have transport mechanisms for taking in dsRNA (see, e.g., Asher, et al. (1969) Nature 223:715–717). Consequently, another delivery option is to administer the dsRNA extracellularly into a body cavity, interstitial space or into the blood system of the mammal for subsequent uptake by such transport processes. The blood and lymph systems and the cerebrospinal fluid are potential sites for injecting dsRNA. Oral, topical, parenteral, rectal and intraperitoneal administration are also possible modes of administration.

The composition introduced can also include various other agents in addition to the dsRNA. Examples of such agents include, but are not limited to, those that stabilize the dsRNA, enhance cellular uptake and/or increase the extent of interference. Typically, the dsRNA is introduced in a buffer that is compatible with the composition of the cell into which the RNA is introduced to prevent the cell from being shocked. The minimum size of the dsRNA that effectively achieves gene silencing can also influence the choice of delivery system and solution composition.

Quantity of dsRNA Introduced

Sufficient dsRNA is introduced into the tissue to cause a detectable change in expression of the candidate gene (assuming the candidate gene is in fact being expressed in the cell into which the dsRNA is introduced) using available detection methodologies such as those described in the following section. Thus, in some instances, sufficient dsRNA is introduced to achieve at least a 5–10% reduction in candidate gene expression as compared to a cell in which the dsRNA is not introduced. In other instances, inhibition is at least 20, 30, 40 or 50%. In still other instances, the inhibition is at least 60, 70, 80, 90 or 95%. Expression in some instances is essentially completely inhibited to undetectable levels.

The amount of dsRNA introduced depends upon various factors such as the mode of administration utilized, the size of the dsRNA, the number of cells into which dsRNA is administered, and the age and size of an animal if dsRNA is introduced into an animal. An appropriate amount can be determined by those of ordinary skill in the art by initially administering dsRNA at several different concentrations for example, for example. In certain instances when dsRNA is introduced into a cell culture, the amount of dsRNA introduced into the cells varies from about 0.5 to 3 $\mu$g per $10^6$ cells.

Detecting Interference of Expression

A number of options are available to detect interference of candidate gene expression (i.e., to detect candidate gene silencing). In general, inhibition in expression is detected by detecting a decrease in the level of the protein encoded by the candidate gene, determining the level of mRNA transcribed from the gene and/or detecting a change in phenotype associated with candidate gene expression.

Various methods can be utilized to detect changes in protein levels. Exemplary methods include, but are not limited to, Western blot analysis, performing immunological analyses utilizing an antibody that specifically binds to the protein followed by detection of complex formed between the antibody and protein, and activity assays, provided the protein has a detectable activity. Similarly, a number of methods are available for detecting attenuation of candidate gene mRNA levels. Such methods include, for example, dot blot analysis, in-situ hybridization, RT-PCR, quantitative reverse-transcription PCR (i.e., the so-called "TaqMan" methods), Northern blots and nucleic acid probe array methods.

The phenotype of the cell can also be observed to detect a phenotypical change that is correlated with inhibition of expression of the candidate gene. Such phenotypical changes can include, for instance, apoptosis, morphological changes and changes in cell proliferation as well as other cellular activities listed supra. Thus, for example, using the neuroblastoma cell line discussed above which serves as a model system for neurological disease studies, one can detect what effect, if any, interference of expression of the candidate gene has on the sensitivity to OGD, β-amyloid and NMDA, for example. If interference with expression of a particular gene relieves one or more of these sensitivities, then therapeutic methods can be developed which involve blocking expression of such a gene. And if interference with expression of a particular gene increases one or more of these sensitivities, then therapeutic methods can be developed which involve activating expression of such a gene.

Alternative Functional Validation Protocols

Methods which combine the library preparation and RNAi techniques described above enables a large number of candidate genes to be analyzed in a high throughput format to determine if the genes play a role in a particular biological state or activity. However, the library preparation methods provided herein can successfully be used in combination with other functional validation approaches, as well. Examples of such approaches follow.

Antisense

Antisense technology can be utilized to functionally validate a candidate gene. In this approach, an antisense polynucleotide that specifically hybridizes to a segment of the coding sequence for the candidate gene is administered to inhibit expression of the candidate gene in those cells into which it is introduced. Methods relating to antisense polynucleotides are well known, see e.g., Melton, D., Ed, 1988, ANTISENSE RNA AND DNA, Cold Spring Harbor Laboratory, Cold Spring Harbor, N.Y.; Dagle et al., 1991, *Nucleic Acids Research*, 19:1805; and Uhlmann et al., *Chem. Reviews*, 90:543–584 (1990).

In general, the antisense polynucleotide should be long enough to form a stable duplex but short enough, depending on the mode of delivery, to be administered in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors. Typically, the antisense polynucleotides used in the functional validation methods comprise an antisense sequence of that usually is at least about 10 contiguous nucleotides long, in other instances at least 12 or 14 contiguous nucleotides long, and in still other instances up to about 100 contiguous nucleotides long, which sequence specifically hybridizes to a sequence from a mRNA encoding the candidate gene.

In some instances, the antisense sequence is complementary to relatively accessible sequences of the candidate gene mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Another useful method for optimizing antisense compositions uses combinatorial arrays of oligonucleotides (see, e.g., Milner et al., 1997, *Nature Biotechnology* 15:537). The antisense nucleic acids (DNA, RNA, modified, analogues, and the like) can be made using any suitable method for producing a nucleic acid, such as chemical synthesis and recombinant methods that are well known in the art.

Gene Knockout Approaches

The functional role that a candidate gene plays in a cell can also be assessed using gene "knockout" approaches in which the candidate gene is deleted, modified, or inhibited on either a single or both alleles. The cells or animals can be optionally be reconstituted with a wild-type candidate gene as part of a further analysis.

Certain "knockout" approaches are based on the premise that the level of expression of a candidate gene in a mammalian cell can be decreased or completely abrogated by introducing into the genome a new DNA sequence that serves to interrupt some portion of the DNA sequence of the candidate gene. To prevent expression of functional protein, simple mutations that either alter the reading frame or disrupt the promoter can be suitable. A "gene trap insertion" can be used to disrupt a candidate gene, and embryonic stem (ES) cells (e.g., from mice) can be used to produce knockout transgenic animals (see, e.g., in Holzschu (1997) Transgenic Res 6: 97–106).

The insertion of the exogenous sequence is typically by homologous recombination between complementary nucleic acid sequences. Thus, the exogenous sequence is some portion of the candidate gene which one seeks to modify, such as exonic, intronic or transcriptional regulatory sequences, or any genomic sequence which is able to affect the level of expression of the candidate gene; or a combination thereof. The construct can also be introduced into other (i.e., non-candidate gene) locations in the genome. Gene targeting via homologous recombination in pluripotential embryonic stem cells allows one to modify precisely the candidate gene of interest.

The exogenous sequence is typically inserted in a construct, usually also with a marker gene to aid in the detection of the knockout construct and/or a selection gene. The construct can be any of a variety of expression vectors, plasmids, and the like. The knockout construct is inserted in a cell, typically an embryonic stem (ES) cell, using a variety of established techniques. As noted above, the insertion of the exogenous DNA usually occurs by homologous recombination. The resultant transformed cell can be a single gene knockout (i.e., only one of the two copies of the candidate has been modified) or a double gene knockout (i.e., both copies of the candidate gene has been modified).

Typically less than one to five percent of the ES cells that take up the knockout construct actually integrate exogenous DNA in these regions of complementarity; thus, identification and selection of cells with the desired phenotype is usually necessary. This can be accomplished by detecting expression of the selection or marker sequence described above. Cells that have incorporated the construct are selected for prior to inserting the genetically manipulated cell into a developing embryo. A variety of selection and marker techniques are well known in the art (e.g., antibiotic resistance selection or beta-galactosidase marker expression). Alternatively, insertion of the exogenous sequence and levels of expression of the endogenous candidate gene or marker/selection genes can be detected by hybridization or amplification techniques or by antibody-based assays.

After selection of manipulated cells with the desired phenotype (i.e., complete or partial inability to express the candidate gene), the cells are inserted into an embryo (e.g., a mouse embryo). Insertion can be accomplished by a variety of techniques, such as microinjection, in which about 10 to 30 cells are collected into a micropipet and injected into embryos that are at the proper stage of development to integrate the ES cell into the developing embryonic blastocyst, at about the eight cell stage (for mice, this is about 3.5 days after fertilization). The embryos are obtained by perfusing the uterus of pregnant females. After the ES cell has been introduced into the embryo, it is implanted into the uterus of a pseudopregnant foster mother, which is typically prepared by mating with vascectomized males of the same species. In mice, the optimal time to implant is about two to three days pseudopregnant. Offspring are screened for integration of the candidate gene. Offspring that have the desired phenotype are crossed to each other to generate a homozygous knockout. If it is unclear whether germline cells of the offspring have modified candidate gene, they can be crossed with a parental or other strain and the offspring screened for heterozygosity of the desired trait.

Further guidance regarding preparation of mice that have a knocked out candidate gene is provided in the following sources, for example: Bijvoet (1998) Hum. Mol. Genet. 7:53–62; Moreadith (1997) J. Mol. Med. 75:208–216; Tojo (1995) Cytotechnology 19:161–165; Mudgett (1995) Methods Mol. Biol. 48:167–184; Longo (1997) Transgenic Res. 6:321–328; U.S. Pat. Nos. 5,616,491 (Mak, et al.); 5,464, 764; 5,631,153; 5,487,992; 5,627,059; 5,272,071; and, WO 91/09955, WO 93/09222, WO 96/29411, WO 95/31560, and WO 91/12650.

Ribozymes

Ribozymes can also be utilized to inhibit expression of candidate gene expression in a cell or animal. Useful ribozymes can comprise 5'- and 3'-terminal sequences complementary to the candidate gene and can be engineered by one of skill on the basis of the sequence of the candidate gene. Various types of ribozymes can be utilized in the functional validation studies, including, for example, those that have characteristics of group I intron ribozymes (see, e.g., Cech, 1995, *Biotechnology* 13:323) and those that have the characteristics of hammerhead ribozymes (see, e.g., Edgington, 1992, *Biotechnology* 10:256).

Ribozymes and antisense polynucleotides can be delivered by a number of techniques known in the art, including liposomes, immunoliposomes, ballistics, direct uptake into cells, and the like (see, e.g., U.S. Pat. No. 5,272,065).

Co-immunoprecipitation

Co-immunoprecipitations can be used to functionally validate the role of a protein in a pathway. If two proteins interact and antibodies are available, co-immunoprecipitations can be used to quickly confirm their role in a pathway.

Alternative Methods for Identifying Candidate Genes

While the functional validation methods (e.g., RNAi methods) disclosed herein have been discussed primarily with respect to candidate genes identified from subtractive and/or normalized libraries prepared according to the methods described supra, it should be understood that these functional validation procedures can be utilized to functionally validate genes that have been identified by any of a number of other methods. For example, the functional validation procedures (e.g., RNAi methods) provided herein can be used to functionally validate low abundance genes and differentially expressed genes identified using other techniques.

These techniques include, but are not limited to, (i) differential display PCR (see, e.g., U.S. Pat. Nos. 5,262,311; 5,5599,672; and Liang, P. and Pardee, A. B., (1992) Science 257:967–971); (ii) nucleic acid probe arrays (see, e.g., WO 97/10365; WO 97/27317; and the entire supplement of Nature Genetics, vol. 21 (1999)); (iii) Quantitative RT-PCR (see, e.g., U.S. Pat. Nos. 5,210,015; 5,538,848; and 5,863, 736); (iv) dot blot analysis; (v) in situ hybridization (see, e.g., Harris, D. W. (1996) Anal. Biochem. 243:249–256; and Sanger, et al. (1986) Singer, et al. Biotechniques 4:230–250); (vi) differential screening methods (see, e.g., Tedder, T. F., et al. (1988) *Proc. Natl. Acad. Sci. USA* 85:208–212); and (vii) other subtractive hybridization methods such as those listed above (see, also, Sargent, T. D. (1987) Methods of Enzymol. 152:423–432; and Lee, et al. (1991) *Proc. Natl. Acad. Sci. USA* 88:2825–2830).

The following examples are provided solely to illustrate certain aspects of the methods that are disclosed herein and are not to be interpreted so as to limit the scope of the application in any way.

EXAMPLE 1

Use of "Knock-Down" Method

A microglia cell line was stimulated with lipopolysaccharide (LPS, 100 ng/ml) and γ-interferon-γIFN-γ, 100 U/ml) in a culture dish. Stimulated and unstimulated cells were harvested at 12 hours and a tester-subtracted library prepared (SL18). In this specific case, the tester and driver dscDNAs were digested with Rsa I, and adaptor set 1 (see Table IV, supra) was used for tester ligations. The first and second hybridizations were for 8 and 16 h, respectively. PCR amplification (primary PCR: 25 cycles, secondary PCR: 12 cycles) was with primer set 1, and products were cloned in pCR 2.1. Primer set 1 is shown supra in Table IV.

To identify sequences useful in the knock-down protocol, randomly chosen clones were submitted for DNA sequencing and sequence results were analyzed using the BlastN algorithm. Of 134 sequences identified by BlastN there were a number of genes represented more than once. Four unique genes were represented multiple times by 5, 5, 5, and 6 redundant clones, respectively, accounting for more than 15% of the BlastN identified sequences. "Knock-down" hybridization matrix analysis proceeded with using these genes as "knock-down" polynucleotides. Another 6,000 colonies from the library was picked, and amplified inserts were arrayed on nylon membranes in triplicate. Membranes were each hybridized to $^{32}$P-labeled tester and driver cDNAs under stringent conditions, signal intensities analyzed by phosphoimaging and ratios of signal intensities calculated.

"Knock-down" of labeled tester cDNAs hybridization signal intensity was accomplished by inclusion of unlabeled "knock-down" polynucleotides during probe denaturation prior to hybridization. As shown in FIG. 1, inclusion of the knock-down polynucleotides resulted in a reduction in signal for redundant clones. In this library, "knock-down" analysis identified 610 clones as redundant, and further analysis (e.g., sequencing) of these genes was thus avoided.

Clones showing at least a 2-fold difference in signal intensities between tester and driver were selected for DNA sequencing and further analysis. Out of the 6,000 original clones in the library, for SL 18 a total of 384 differentially regulated clones were identified. The results of sequence analysis of these clones up-regulated by LPS/IFN-γ, is shown in Table XI:

TABLE XI*

| Library | Known Genes | Similar Genes | Unknown Genes |
| --- | --- | --- | --- |
| SL18 | 52% | 22% | 26% |

*Gene classification is based on BlastN results using the most recent version of Genbank as database. Genes are considered to be "known" if they display a high degree of similarity (>80% identity on nucleotide level)) to a database entry, as similar if they display a distant similarity (40–80% identity on nucleotide level) and as unknown if they do not show any homology or an insignificant homology to a database entry.

The identification, in this experiment, of redundant clones demonstrates the utility of this method for efficient high-throughput analysis of a large number of genes. In addition, the large number of unknown genes identified is a further validation for the completeness of the analysis.

EXAMPLE 2

Knockdown Selection of Redundant Clones

A mouse microglial cell line known to respond to stimulation by incubation in media containing lipopolysaccharide (LPS) and gamma interferon (γIFN) was used. mRNA was purified from cells before (=driver) and after stimulation (=tester). A normalized and subtracted cDNA library was prepared and cloned in bacteria ("Library 1").

For a representative number of clones (670), sufficient sequence was determined to assign a Genbank identifier tag (GID) based on a BLAST comparison. Clones matching a GID for MERANTES (GID X70675) were highly represented in the sample (10 clones of 670, or approximately 1.5%). DNA corresponding to the MERANTES sequence was amplified by PCR to produce "knockdown cDNA."

Radiolabeled cDNA probes were prepared from approximately 0.5 micrograms of tester or driver mRNA. The knockdown cDNA was boiled 5 minutes, cooled on ice, and approximately 1 microgram was added to aliquots of radiolabeled tester probe. Equivalent aliquots of radiolabeled tester probe and driver probe were used without the addition of knockdown cDNA. The probe or probe/knockdown mixtures were incubated at 68° C. for 20 minutes and hybridization solution 50% formamide, 5×SSC, 5×Denhardt's reagent, 1% SDS, 0.025% sodium pyrophosphate) was added.

Each of the probe mixtures was hybridized to nylon membranes onto which PCR-amplified cDNA prepared from the 670 partially sequenced clones from Library 1 had been spotted. Hybridization was for 20 hours at 42° C. and was followed by washing and signal detection.

Quantitation of the signal level of tester, knockdown-tester and driver hybridizations allowed the selection of clones upregulated by LPS and γIFN, based on their tester/driver ratios. Further, the signal ratio of tester/knockdown-tester allowed for the identification of clones that match the knockdown cDNA. All 10 clones corresponding to MERANTES were identified by an elevated tester/knockdown-tester ratio, with an average tester/knockdown-tester signal ratio of 6.4 fold (stdev 2.2). In contrast, the average tester/knockdown-tester signal ratio for all clones was 1.38 (stdev 0.7). There was one clone with tester/knockdown-tester ratio above 3 fold that was not MERANTES. The selection and effort of further handling of redundant clones (e.g. MERANTES) can be reduced by rejection of clones having an elevated tester/knockdown-tester ratio (e.g. greater than 3)

EXAMPLE 3

Improved Method for Evaluating Quality of Normalized and Subtracted cDNA Libraries A. Preparation of Tester and Driver ds cDNA Human fibroblasts (ATCC CRL 2091) were grown to approximately 60% confluence in 15 cm Petri dishes in Dulbecco's Modified Eagle Medium (DMEM), 10% Fetal Calf Serum (FCS). The cells were washed 3 times with DMEM lacking FCS. After a 48 hour incubation in DMEM with 0.1% FCS the medium was replaced with fresh medium containing 10% FCS (serum stimulation). Cells were collected at two different time points. One batch of cells was collected just prior to serum stimulation (serum stimulated cells). This sample served as a time zero reference from which "driver" RNA was prepared. Another batch was collected 6 hours after the addition of FCS. This sample served as a stimulated sample from which "tester" RNA was prepared (serum starved cells).

Total RNA from these samples was prepared using Trizol (Life Technologies). mRNA was selected using Oligotex Kit (Quiagen). The poly A$^+$ RNA was reverse transcribed using an Oligo dT priming method and converted into double-stranded cDNA (dscDNA) using standard methods.

B. Preparation of Normalized and Subtracted Libraries

The ds cDNA was digested with Rsa I (NEB). The Rsa I-digested tester and driver ds cDNA were divided into two aliquots each, and each aliquot was ligated to an adapter oligonucleotide (Adapter set No. 1, shown in Table IV, supra). The ligation reaction was performed for 12 hours at 16° C. using T4 DNA Ligase (2000 U/µl).

Normalized-subtracted and normalized libraries were prepared as described in §D and E, supra, respectively, using different tester/driver ratios and different conditions for the two annealing steps, as summarized in the table below

| Library ID | Library Description | Ratio Tester/driver | Annealing time (First annealing step) | Annealing time (Second annealing step) |
|---|---|---|---|---|
| A | Driver-Normalized | 1:5 | 9 hours | 18 hours |
| B | Tester-Normalized | 1:5 | 9 hours | 18 hours |
| C | Normalized-Subtracted, Tester-Subtracted | 1:5 | 9 hours | 18 hours |
| D | NORMALIZED-SUBTRACTED, Tester-Substracted | 1:15 | 9 hours | 18 hours |
| E | NORMALIZED-SUBTRACTED, Tester-Subtracted | 1:10 | 9 hours | 18 hours |
| F | NORMALIZED-SUBTRACTED, Tester-Subtracted | 1:10 | 12 hours | 18 hours |
| G | NORMALIZED-SUBTRACTED, Tester-Subtracted | 1:10 | 12 hours | 36 hours |
| H | NORMALIZED-SUBTRACTED, Driver-Subtracted | 1:20 | 9 hours | 18 hours |
| I | NORMALIZED-SUBTRACTED, Driver-Subtracted | 1:10 | 9 hours | 18 hours |
| J | NORMALIZED-SUBTRACTED, Driver-Subtracted | 1:10 | 12 hours | 18 hours |
| K | NORMALIZED-SUBTRACTED, Driver-Subtracted | 1:10 | 12 hours | 36 hours |

Following annealing, a 2-step (nested) PCR amplification was performed to isolate sequences of interest. In the first PCR reaction only molecules which different adapter sequences on each end are amplified exponentially by the adapter-specific primer PCR1. The number of PCR cycles needed to obtain sufficient amounts of amplicon for analysis depends on the experimental paradigm under investigation, and needs to be determined empirically by performing the PCR amplification procedure with different cycle numbers and analyzing amplicon yields (e.g., by agarose gel electrophoresis). In this analysis, different numbers of PCR cycles (21, 23, 25 and 27) were used for the first PCR amplification whereas the second, nested PCR amplification using nPCR1 and nPCR2 as primers proceeded with 12 cycles for all samples.

PCR primer for first amplification: PCR1, (SEQ ID NO:14) CTAATACGACTCACTATAGGGC; PCR primer pair for second, nested amplification:

```
nPCR1, TCGAGCGGCCGCCCGGGCAGGT    (SEQ ID NO:15)

nPCR2, AGCGTGGTCGCGGCCGAGGT     (SEQ ID NO:16)
```

C. Evaluation of Library Quality
i) Array Preparation

Arrays can be prepared using various materials and protocols (for examples, see Schena, Mark et al., "Quantitative monitoring of Gene Expression patterns with a complementary DNA microarray", Science (1995) v270:467–470, and Zhao, Nanding et al., "High-Density cDNA Filter Analysis: A Novel Approach for Large-Scale, Quantitative Analysis of Gene Expression", Gene (1995) v156:207–213). An array can be comprised of a large number of clonal cDNAs on a substrate. The cDNAs can be produced by various methods, including purification of plasmids and PCR amplification. The cDNAs are commonly attached by treatment with heat, ultraviolet light, chemicals or enzymes, or by reaction with a preactivated surface. One typical array starts with the PCR amplification of 11520 bacterial clones containing cDNAs inserted into a plasmid. These clones are commonly from a normalized-subtracted library and therefor contain genes differential in tester and driver mRNA expression levels. Aliquots of the PCR reactions are spotted onto nylon membrane (Scheicher & Scheull) to produce the array. To this array various standard genes are added, the cDNA fragments are denatured by wetting the membrane in a solution of 0.5M sodium hydroxide, 1.5M sodium chloride to allow better availability for hybridization, neutralized and crosslinked by ultraviolet light (Stratalinker, Stratagene). A particular example of a cDNA array suitable for analysis of library production methods was prepared. Clones corresponding to 80 genes were selected because their mRNA expression levels in fibroblasts varied upon stimulation by serum, based on cDNA microarray data as described in Iyer, Vishwanath et al., 1999 Science v283:83–87, incorporated herein by reference in its entirety for all purposes. Recombinant clones were purchased from Research Genetics and verified by DNA sequencing. The cDNA insert of each clone was PCR-amplified using vector-specific primers. PCR products were verified by gel electrophoresis. PCR products were spotted in sextuplicate on nylon membranes.

ii) Probe Preparation ds cDNA from each of libraries A–K described supra (i.e., the products of the second PCR amplification) were gel purified using a QiaEx Gel purification kit. The purified products were labeled with $^{32}$P-dCTP (Klenow, Decamer labeling Kit, Ambion) and unincorporated nucleotides were removed by spin column P30 (BioRad).

iii) Evaluation of Library Quality

The probes were hybridized to the cDNA arrays at 42° C. in 5×SSC/50% formamide for 20 hours. The hybridized arrays were washed in 0.1×SSC at 60° C. and exposed to phosphorimager screens (Packard Instruments) for approximately 64 h. Hybridization signal intensities were determined by a Cyclone scanner and Optiquant software (Packard Instruments), normalized by controls including genomic DNA standards, and comparisons were made between serum-starved fibroblasts (=driver), serum-stimulated fibroblasts (=tester) and different normalized and subtracted libraries. Signal intensity of filter hybridizations was used to determine the abundance of genes and gene fragments in the material used to make the probe (see NUCLEIC ACID HYBRIDIZATION, A PRACTICAL APPROACH, pp. 21–22 and 77–111, Hames B D and Higgins S J eds., IRL Press (1985), and Kafatos et al., 1979, Nucleic Acids Research Res., 7, 1541).

Analysis of the quantified hybridization signal from the arrays allowed grouping of the arrayed genes into several classes based on signal intensities after hybridization. These classes were called low, medium, or high signal levels (herein, corresponding to clones with approximate signal levels of less than 5000 Digital Light Units or DLU=low, 5000–16000 DLU=medium, greater than 16000 DLU, corresponding to the intensity of the original radioactive probe hybridized to each spot of cloned cDNA on the array). The arrayed genes were also grouped into classes that increase, maintain, or decrease signal intensity (were regulated in the amount of mRNA produced under condition of tester and driver(e.g., serum-stimulation and serum-starvation). In this example, genes were considered up-regulated if the ratio of their tester/driver signals is greater than 2, genes are considered unchanged if the ratio of their tester/driver signals were greater than 0.85 and less than 1.15, and genes were considered down-regulated if the ratio of their driver/tester signals is greater than 1.5. For example, gene could be of low abundance in driver (i.e. low signal of hybridization, herein less than 5000 DLU) and upregulated (i.e. ratio of tester/driver signals is greater than 2).

Figure 2:
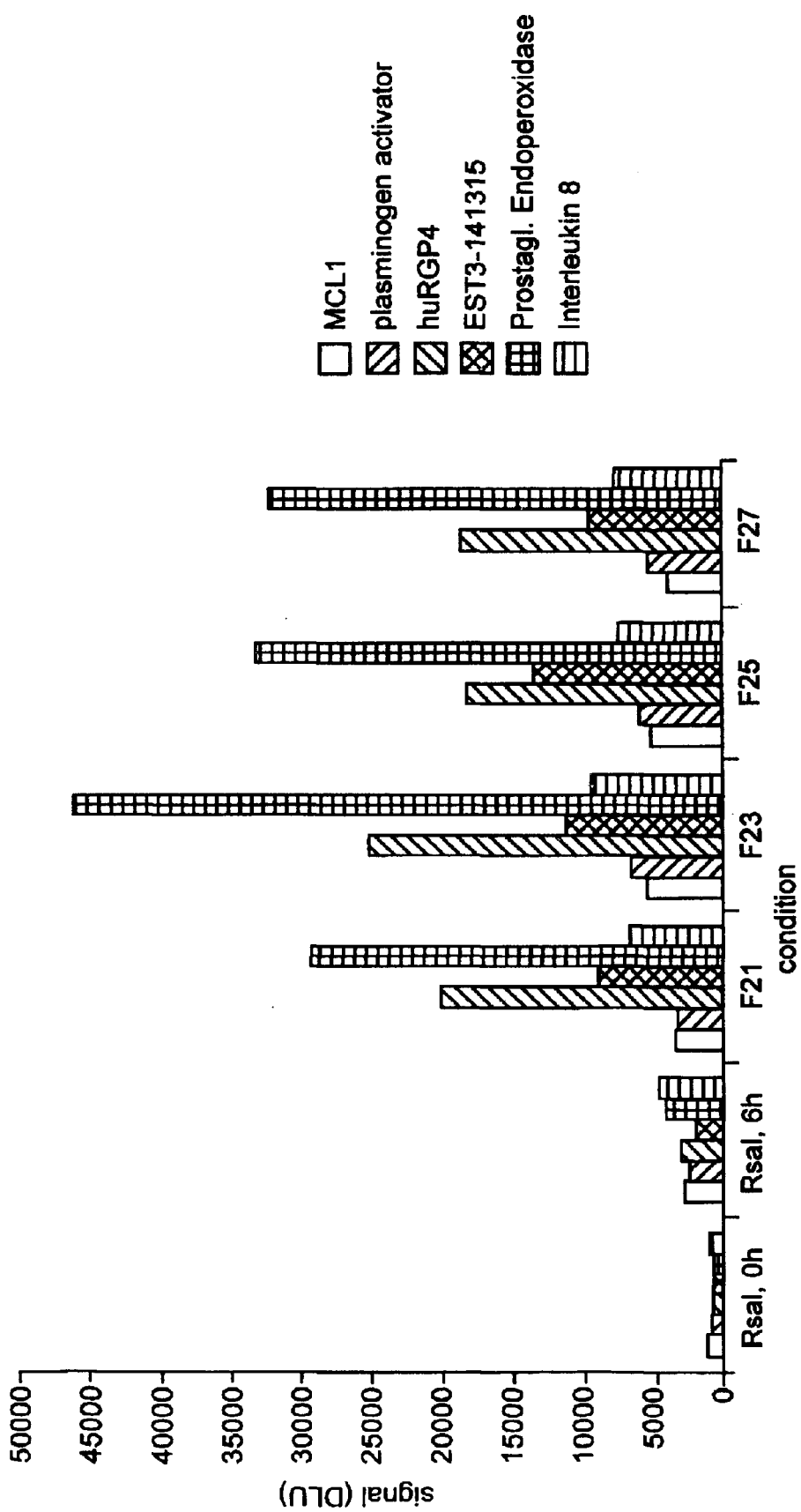
FIG. 2. Clones representing a group that are upregulated in Rsa I, 6 h (tester) as opposed to Rsa I, 0 h (driver) and are of low hybridization signal (=low abundance) in tester and driver are increased in their signal (abundance) under condition of Library ID "F" (normalized tester-subtracted) and PCR cycles=21, 23, 25, 27. Libraries (L) and numbers of amplification steps in the second PCR cycle (N) are indicated by the shorthand "LN." For example, "A21" encodes a description of Library ID "A" with second PCR cycle process length of 21 cycles.
Figure 3:
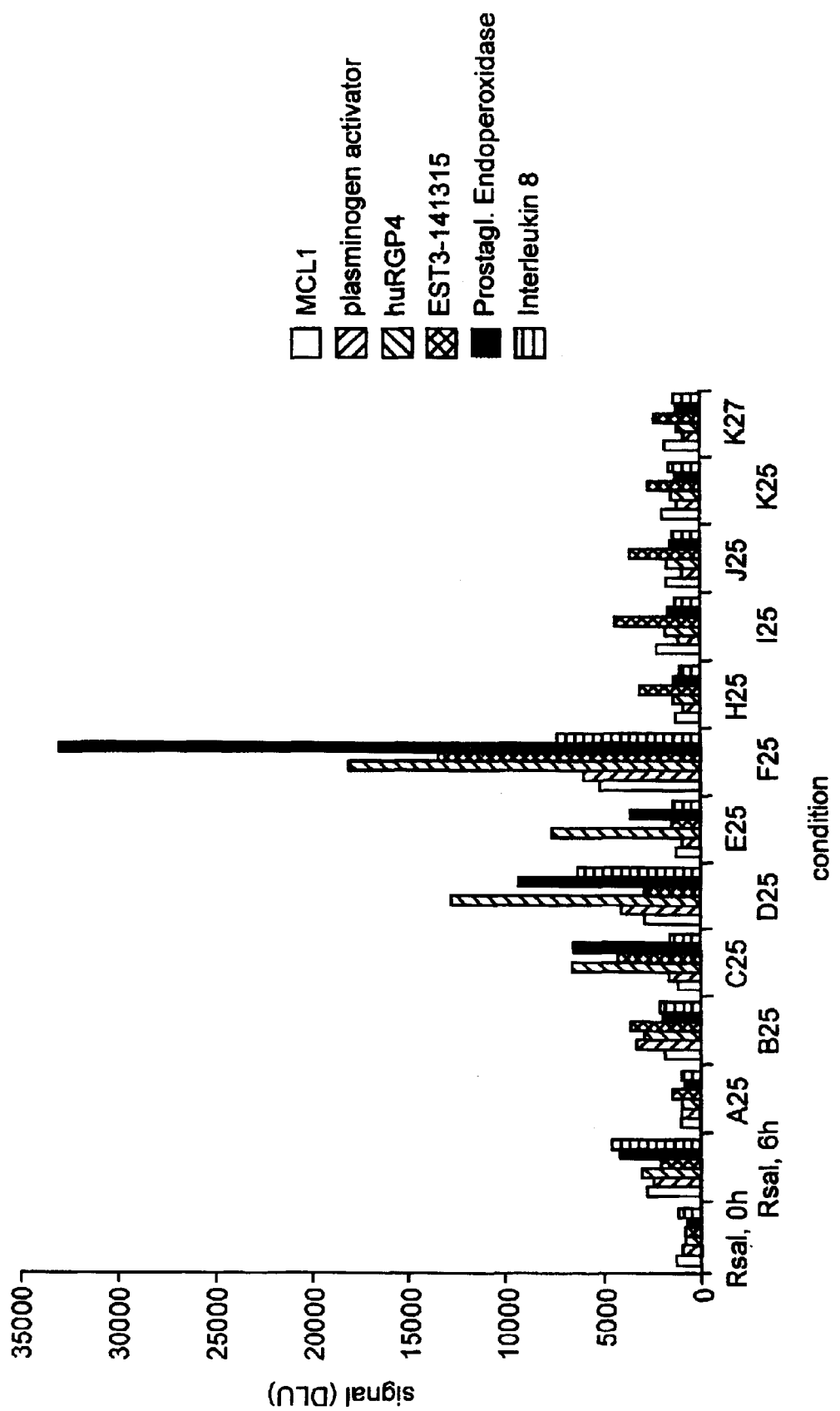
FIG. 3. Clones representing a group that are upregulated in Rsa I, 6 h (tester) as opposed to Rsa I, 0 h (driver) and are of low hybridization signal (=low abundance) in tester and driver are increased in their signal (abundance) under condition of Library IDs "C" through "F" (normalized tester-subtracted), "H" through "K" (normalized driver-subtracted) and PCR cycles=25. Clones from Library IDs "A" and "B" are essentially unchanged.
Figure 4:
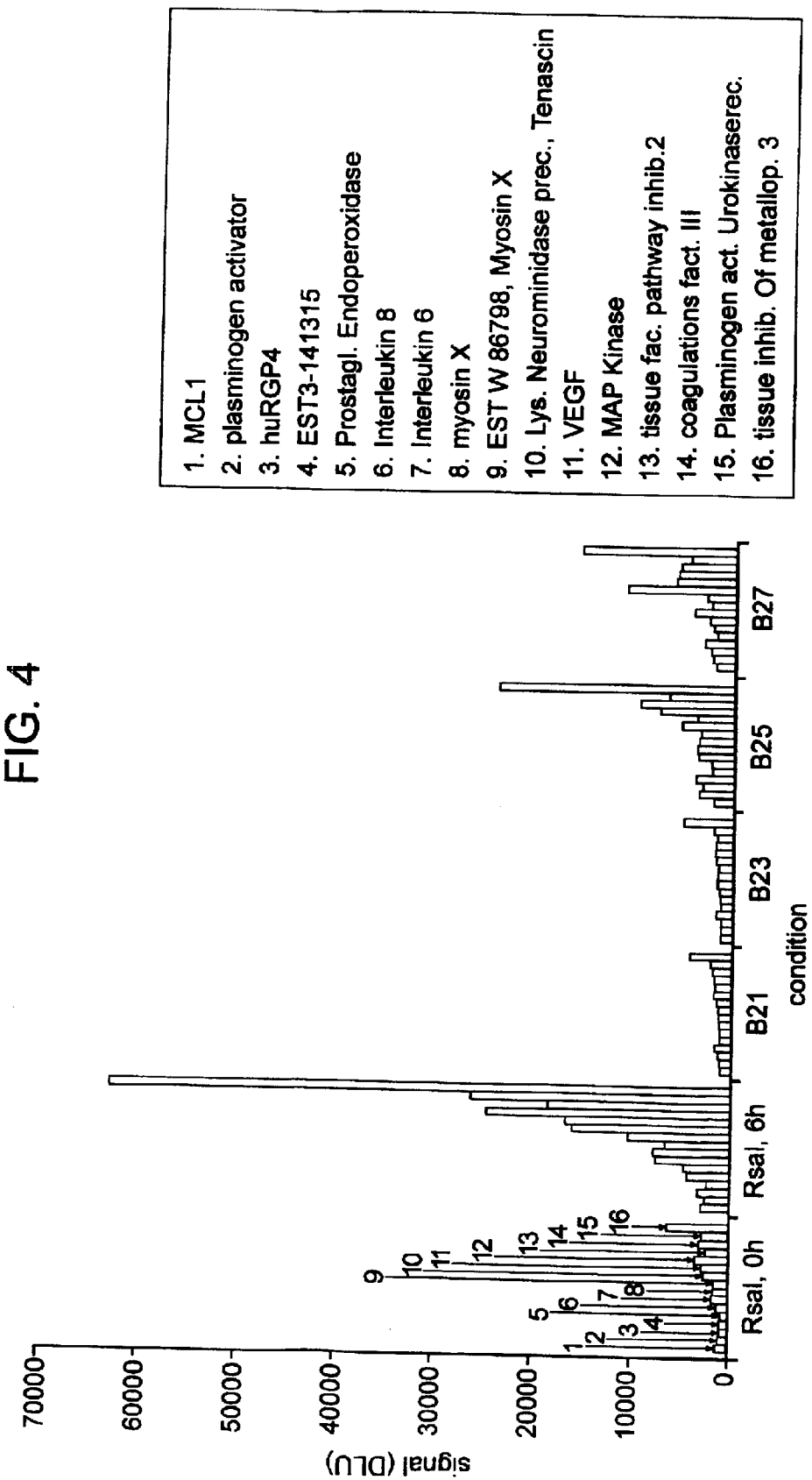
FIG. 4. Clones representing groups that are upregulated in Rsa I, 6 h (tester) as opposed to Rsa I, 0 h (driver) and are of low, medium or high tester hybridization signal are normalized in their signal under condition of Library ID "B".

In FIGS. 2–4, selected clones within the different abundance classes illustrate the effect of condition group (Library ID) and PCR cycle length (e.g., 21, 23, 25, or 27 cycles on the representation of the clone in the library. For reference, hybridization values for control (=driver) probe are marked RsaI, 0 h, and serum stimulated (=tester) probe are marked RsaI, 6 h are included in each graph.

This analysis allowed the determination of enrichment factors for each clone represented on the cDNA array and each normalized and subtracted cDNA library. The enrichment factors describe the change in abundance of a particular gene in normalized and subtracted cDNA libraries and are indicators for the success/quality of that library. The quality of a normalized-subtracted library is assessed by the degree to which differentially expressed genes are enriched in the library. During Tester-Subtracted subtraction, upregulated genes (of abundance higher in tester than in driver) are increased in abundance in the resulting library, and down regulated genes are decreased. During reverse subtraction, the reverse is true (e.g. down regulated genes are increased in abundance in the resulting library). The data show that particular conditions (e.g. F25) can increase further the signal and abundance of low, medium and high abundance genes where their initial abundance are higher in tester than in driver.

The quality of a tester-normalized or driver-normalized library is assessed by the degree to which sequences in the library are present in the same abundance, as assessed by a similar intensity of hybridization to the arrayed clones. In a perfectly normalized library, all of the sequences represented are present in the same abundance. Normalization of the abundance of clones gives a more equal chance of discovering what were initially abundant and non-abundant genes, saving time by reducing redundancy of the clone fragments. The data show that particular conditions (e.g. library B) can increase further the signal and abundance of low, medium and high abundance genes where their initial abundance are higher in tester than in driver.

The quality of a tester-subtracted normalized library is demonstrated by an increase in the occurrence of genes that are more abundant in tester than in driver, a decrease in the occurrence of genes that are more abundant in driver than tester, and the abundance of genes that remain in the library are normalized. This leads to an increase in the abundance of genes having a low abundance that are more prevalent in tester than driver. The normalization will also decrease the redundancy of very abundant genes that are more prevalent in tester than driver. This effect of normalization will ease the discovery of genes more specific to tester that are rare, and increase the efficiency of identifying all genes in the subtracted library. An equivalent assessment of quality can be made for a driver-subtracted normalized library.

EXAMPLE 4

Double-Stranded RNA Transfection Blocks eGFP Expression in Neuroblastoma Derived Cells This experiment was undertaken to determine the level of gene specific silencing that could be achieved in certain neuroblastoma cell lines using RNAi techniques as described herein. The AGYNB-010 cell line utilized in this particular investigation was derived from a neuroblastoma cell line called Neuro 2A (ATCC No. CCL131). As described further below, the AGYNB-010 cell line was shown by the current inventors to be sensitive to OGD, NMDA and β-amyloid relative to the Neuro 2A cell line. The sensitivities exhibited by the AGYNB-010 cell line makes the cell line a good model system for studying various neurological and non-neurological conditions such as ischemia, excitotoxicity, Alzheimer's disease and oxidative stress because these conditions are associated with the foregoing sensitivities. The AGYNB-010 cell line were transfected with a green fluorescent protein (GFP) expressing plasmid to provide an assay system to determine the reduction in specific protein levels achieved by RNAi rapidly and quantitatively.

Materials and Methods

Generation of a neuroblastoma derived cell line expressing the enhanced Green Fluorescent Protein (eGFP). Neuro 2A cells were grown in DMEM and then plated in a six well plate at a concentration of $5 \times 10^5$ cells/ml. A plasmid expressing eGFP was obtained from Clontech(pEGFP-CI). Twenty-four hours after seeding the plates with Neuro 2A cells, the cells were co-transfected with 0.5 microgram of pCMVneo (available from Stratogene) and three microgram of pEGFP-CI. Forty-eight hours after cotransfection, cells were transferred to media containing G418 to select for transfected cells. Cells resistant to G418 were selected, tested for GFP by visualization with a light microscope, replated and independent clonal lines established. The established cell line was further tested for OGD, β-amyloid, and NMDA sensitivity according to the assays set forth below in this section.

High throughput RNA transcription. Single strands of sense and anti-sense RNA from the full length pEGFP clones were transcribed about 500 bp of EGFP-C (i.e., about 500 bp of the C-terminus of the pEGFP) in vitro using T3 and T7 promoters. Addition of SP6 polymerase results in the transcription of sense RNA, and addition of T7 polymerase results in the transcription of antisense RNA (Ambion). Transcripts were purified of proteins using phenol-chloroform extraction. RNA was precipitated by adding 20 microliters of 10 M ammonium acetate and 220 microliters of isopropanol to 200 microliters of the extracted mix and then incubating the resulting mixture at −20° C. for 15 minutes. The mixture was centrifuged and the RNA pellet dried and resuspended in 100 microliters of RNAse free double distilled water. The concentration of RNA was determined to be approximately 1 microgram/ml. The length of the transcripts was typically 500 bases or more.

For use as control, dsRNA corresponding to the full length coding region of UCP-2 (uncoupling protein 2) gene was prepared in a similar manner.

In vitro transcription can also be done in 96-well format using both T3 and T7 promoter to generate sense and antisense strands. Purification of the transcripts is done using RNA purification columns, such as, but not limited to, RNeasy kit (available from Qiagen). Annealing of both strands in the absence of potassium chloride or sodium chloride can be achieved using ammonium acetate, e.g., at about 10 μM to 1 mM concentration. The reaction buffer is then adjusted to 500 mM of sodium chloride before RNase T1 treatment. RNase T1 is added to degrade any non annealed single-stranded RNA. The resulting products are passed through RNA purification columns again to remove RNase T1. Concentration of the final dsRNA products can be measured using a plate reader.

Synthesis of Double-stranded RNA. Equimolar quantities of sense and antisense RNA strands from either eGFP or UCP-2 were added in a reaction solution of annealing buffer; annealing of the sense and antisense strands was carried out by incubation at 60° C. for thirty minutes and then allowed to cool at room temperature. A variety of annealing buffers can be used. For example, when an annealing solution containing 20 mM sodium chloride is used, the reaction mixture is heated incubated at 60° C. for thirty minutes and cooled for about 15 minutes to afford a dsRNA. Alternatively, the RNA can be added to 10 mM Tris (pH 7.5) buffer containing 20 mM of sodium chloride. The mixture is incubated for 95° C. for about one minute and cooled at room temperature for about 12 to 16 hours to afford a dsRNA. In another embodiment, the RNA is precipitated in 1 M ammonium acetate solution and resuspended in double distilled water. The mixture is then incubated at 60° C. for thirty minutes and cooled for about 15 minutes to afford a dsRNA. The latter buffer solution differs from annealing buffers used by others which contain potassium or sodium chloride. The approach described here also differs from other approaches in that incubation typically is only for 30 minutes, whereas the others typically incubate the mixture overnight (see, e.g., Tuschel et al., *Genes and Dev't*, 1999, 13, 3191–3197)

Transfection of double-stranded RNA into cells. AGYNB-010 cells were plated in six well plates at a density of 3–4×10$^5$ cells/ml in DMEM containing 10% fetal bovine serum(Sigma). Twenty-four hours later, the AGYNB-010 cells were washed in serum free DMEM in preparation for transfection. Two separate solutions were prepared: Solution A contained 1–5 micrograms of double-stranded GFP RNA or control RNA (UCP-2 RNA) and 100 micoliters of serum free DMEM. Solution B was prepared by diluting Lipofectamine(Gibco BRL) with serum free DMEM (9:1 ratio). Solution A and B were gently mixed and incubated for 15 minutes at room temperature, then 0.8 ml of serum free DMEM was added to the transfection mixture and this mixture overlayed on the washed cells. Care was taken to ensure that the final volume of the transfection mixture overlayed on the cells did not exceed 1 ml. The cells were incubated at 37° C. in a $CO_2$ incubator for 18–24 hours. The cells are drained of the transfection mixture and replaced with fresh DMEM containing 10% FBS.

Measurement of the Level of Gene Specific Silencing

Direct fluorometry: Two days after transfection, 10$^6$ AGYNB-010 cells transfected with either eGFP dsRNA or UCP-2 dsRNA were seeded on a plate and the amount of green fluorescence quantitated by using a cytofluor plate reader (e.g., Series 4000, Perseptive Biosystem).

Western Blot analysis: Two to five days after transfection, cell extracts from AGYNB-010 cells transfected with either eGFP dsRNA or UCP-2 dsRNA were harvested in standard RIPA buffer and the total protein concentration determined using the BCA assay system from Pierce. Thirty micrograms of total protein from the cell extracts was loaded per lane on an SDS-PAGE gel. The gel was transferred to nitrocellulose using standard western transfer procedures. GFP protein was detected using anti-GFP from Chemicon. The level of microtubule associated protein-2 (i.e., MAP2), a non specific protein, was used as a loading control. Anti-MAP2 was obtained from Sigma. The western blot was then scanned in and quantified using NIH image.

Methods for Detecting Various Cell Sensitivities

Oxygen-glucose deprivation (OGD). To measure the sensitivity of cells to combined oxygen-glucose deprivation, cells were resuspended in glucose free deoxygenated media (Earle's balanced salt solution (EBSS) containing 116 mM NaCl, 5.4 mM KCl, 0.8 mM $MgSO_4$, 1 mM $NaH_2PO_4$, and 0.9 mM $CaCl_2$) bubbled with 5% $H_2$/85% $N_2$/5% $CO_2$. the cells were transferred to an anaerobic chamber for 5 or 60 min at 37° C., containing the following gas mixture, 5% $H_2$, 85% $N_2$, and 5% $CO_2$. At the end of the incubation period, oxygen glucose deprivation was terminated simply by removing the cells from the anaerobic chamber and replacing the EBSS solution with oxygenated growth media. Sensitivity of the cells to OGD was determined by measuring cell death. The cells were stained with calcein and ethidium homodimer (Molecular Probes), which stains live cells and dead cells, respectively, the staining quantitated on a cytofluor plate reader, and the percentage of dead cells determined. One can also use any of the other conventional methods known to one skilled in the art to determine cell health.

NMDA Sensitivity. Cells were washed with control salt solution (CSS) containing 120 mM NaCl, 5.4 mM KCl, 1.8 mM $CaCl_2$, 25 mM Tris-HCl, 15 mM glucose, pH 7.4. N-Methyl-D-aspartic acid (NMDA) was applied in CSS for 5 min, and after this incubation time the NMDA solution was removed from the cells and growth medium. Toxicity was assayed 20–24 hrs. after exposure to NMDA solution.

β-Amyloid Sensitivity. Cells were plated the day before exposure to either β-amyloid or peroxide in a 24 well plate at a concentration of 1×10$^5$ cells/well. To measure sensitivity to β-amyloid, cells were exposed to 1–50 μM β-amyloid for 24–72 hours using CSS solution described above for NMDA sensitivity test. β-Amyloid was made by first solubilizing it in DMSO or an aqueous solution and the resulting solution then diluted in DMEM. In both instances, sensitivity was assessed by measuring cell death using the staining procedure described in the section on assays for OGD.

Results

FIG. 5 shows the results of a Western Blot analysis. Lanes 1 and 2 of the gel show eGFP and MAP2 protein levels for untransfected cells (i.e., "mock" cells). However, lanes 6–8 show a significant reduction in eGFP levels for AGYNB-010 cells transfected with 3 μg of eGFP-C dsRNA; likewise, cells transfected with 3 μg of enhanced green fluorescent protein (i.e., eGFP) dsRNA also showed a significant reduction in eGFP levels (lanes 9–10). The results demonstrate selectivity in inhibition in that eGFP expression is inhibited by eGFP dsRNA but not UCP-2 dsRNA. The consistent bands for MAP2 across all lanes confirms consistency in protein loading.

Figure 7A:
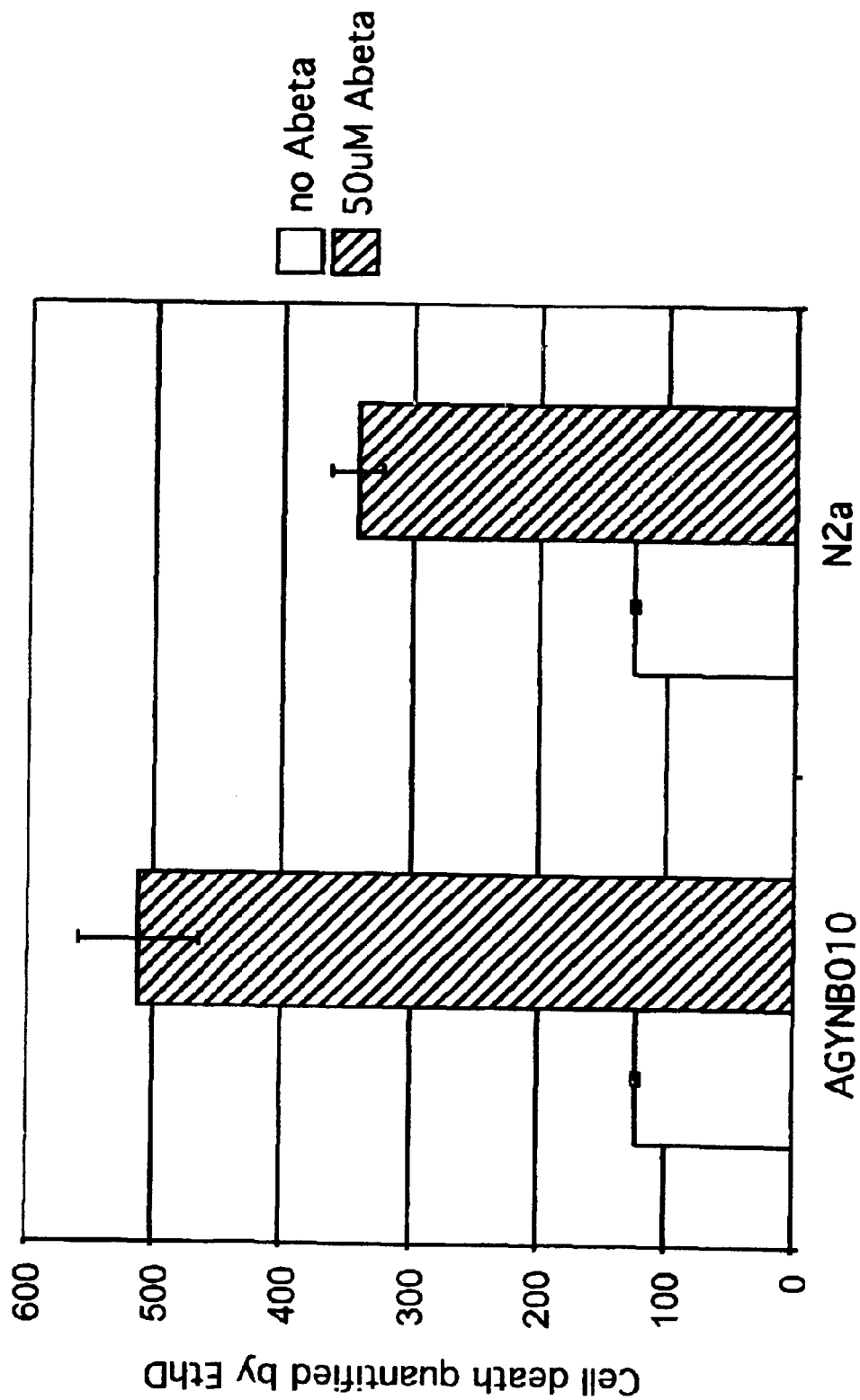

The AGYNB-010 neuroblastoma derived cell line was shown to be sensitive to β-amyloid, NMDA and OGD as compared to Neuro 2A cells from which the AGYNB-010 cells are derived (see FIGS. 7A, 7B and 7C, respectively). As indicated supra, these sensitivities mean this particular cell line can serve as a useful model for conducting studies of various biological phenomenon associated with such sensitivities. For instance, the cell line can be used in studying stroke (e.g., ischemic stroke), as stroke is associated with oxygen deprivation.

EXAMPLE 5

Double-Stranded PARP RNA Blocks Endogenous PARP Expression

Ischemic stroke results from transient or permanent reduction of the cerebral blood flow. Neuronal cells require high oxygen levels for viability and normal function. Deprivation of oxygen thus leads to neuronal death causing brain damage. In contrast, shorter exposures to ischemia result in protection from neuronal damage, a phenomena known as ischemic tolerance, or ischemic preconditioning. PARP (poly-ADP-ribose-polymerase) is a gene that is up-regulated in ischemia. Thus, PARP inhibitors or inhibition of PARP may have neuroprotective effects. As demonstrated in Example 4, AGYNB-010 cells are sensitive to oxygen glucose deprivation and thus provide a sensitized system for studying ischemia.

Transfection of dsRNA into cells. Single strands of sense and anti-sense RNA from the C terminus or N terminus of the PARP gene (NM_007415, e.g., PARP-N 79–1171 and PARP-C 2200–2797 regions) or from UCP-2 as control were transcribed, purified and concentrated according to the general procedure set forth in Example 4. The single strands were converted to dsRNA and then transfected into AGYNB-010 cells also as described in Example 4.

Measurement of the level of gene specific silencing. Cells transfected with UCP-2 dsRNA (dsUCP-2), PARP dsRNA from the C terminus (dsPARP-C), or PARP dsRNA from the N-terminus (dsPARP-N) were harvested and analyzed by Western blot according to the protocol described in Example 4. PARP protein was detected using anti-PARP from Oncogene.

Assays for resistance to cell death. AGYNB-010 cells that were untransfected, transfected with eGFP dsRNA (see Example 4) or transfected with PARP dsRNA, were assayed for their sensitivity to oxygen glucose deprivation. Sensitivity was measured using the cell death assay described in Example 4.

Results and Discussion

As observed in FIG. 6A, AGYNB-010 cells transfected with dsPARP RNA from either the C terminus (lanes 3–6) or N terminus (lanes 7–10) show significant reduction in endogenous PARP levels. Endogenous PARP levels are not affected by transfection with dsUCP-2 (lanes 1–2), thus demonstrating the ability to selectively inhibit a target gene by introducing a dsRNA corresponding to the target gene.

Figure 6B:
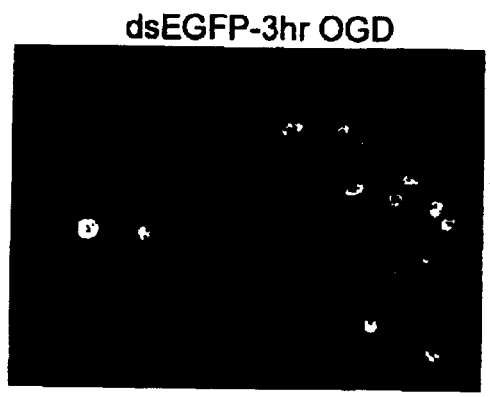
FIGS. 6B–6D. Results showing that RNAi mediated inhibition of PARP expression induces resistance to oxygen glucose deprivation (OGD).
Figure 6C:
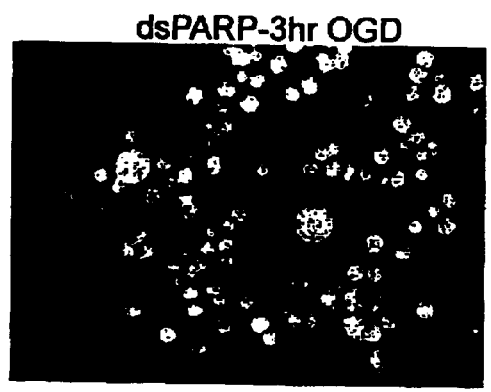
Figure 6D:
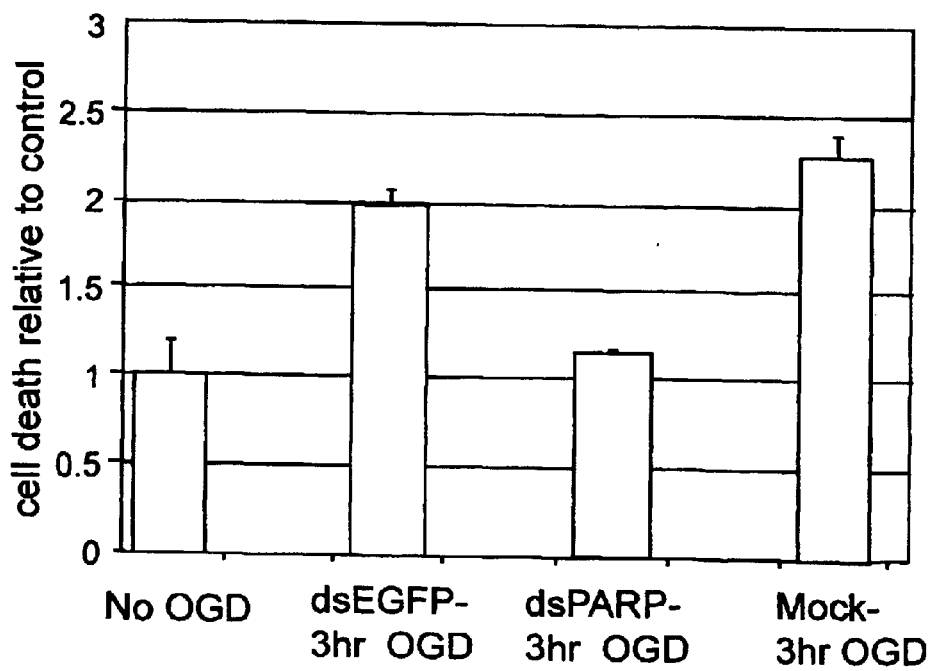

The RNAi mediated inhibition of PARP also induces resistance to OGD as observed by determining the cell death. FIG. 6B is a view showing the number of stained cells (i.e., healthy cells) present for cells transfected with dsEGFP 3 hours after the start of oxygen glucose deprivation. FIG. 6C, shows a similar view of cells similarly treated, except the cells are transfected with dsPARP. FIG. 6D is a chart showing the same results as in FIGS. 6B and 6C. The chart also shows results for two controls: (1) the extent of cell death for cells not exposed to OGD, and (2) mock cells (i.e., untransfected cells) subject to 3 hours of OGD. Collectively, these results show the ability of dsPARP to rescue cells having been previously subjected to 3 hours of OGD.

Thus, these functional validation results obtained by RNAi are consistent with the gene expression data indicating that up-regulation of PARP is correlated with harmful cellular effects caused by ischemia. The results with the model system provided herein indicate that inhibition of PARP can provide a neuroprotective effect, particularly against ischemia. This makes PARP an attractive target for treatment of stroke.

EXAMPLE 6 dsRNA to Inhibit Gene Expression

To demonstrate whether long dsRNA mediates gene-specific silencing in mouse neuroblastoma N2a cells, cell lines were generated expressing EGFP stably (N2a-EGFP) to mimic the expression of an endogenous gene. dsRNA corresponding to the full-length (dsEGFP) or to the C-terminal part of the EGFP (dsEGFP-C) open reading frame was generated for transfection into these N2a-EGFP cells. Control dsRNA was made from the entire coding region of the uncoupling protein-2 (UCP2). N2a-EGFP cells were plated 24 hours before transfection. In most cases, 5 nM of the double-stranded RNA was transfected using Lipofectamine (Invitrogen) per manufacture's instructions. The cells were incubated in the LipofectAmine complex overnight, after which normal media was added and cells were incubated for 4 additional days. The fluorescence decreases significantly in cells transfected with dsEGFP compared with those transfected with dsUCP-2 and mock transfected controls. Western blot shows that both dsEGFP and dsEGFP-C decrease the EGFP protein level significantly without affecting the expression of the housekeeping gene MAP-2 (FIG. 8A). dsEGFP inhibited EGFP expression in a dose-dependent manner, with 5 nM showing the maximum effect (FIG. 8B).

In this series of experiments, the reporter gene EGFP was used to facilitate detection of expression. However, unlike other studies in which the expression plasmid coding for the reporter gene was cotransfected with dsRNA, dsRNA was transfected into a stable cell line expressing EGFP protein that mimics expression of endogenous genes. The dsRNA-induced inhibitory effects we observed were clearly gene-specific. Control dsRNA corresponding to an unrelated gene show non-significant suppression of EGFP expression compared with mock-transfected. Furthermore, cells remain alive and healthy with no significant apoptosis induced by transfection of double-stranded RNA. These experiment also show that both long and short dsRNA has an effect on expression.

Studies have shown that short, siRNA of 21 nt can induce efficient gene-specific silencing in mammalian cells. In N2a cells, it is demonstrated herein that siRNA derived from FASTK ORF indeed induced gene-specific silencing, confirming the efficacy of siRNA in these neuronal cells. However, higher concentrations of siRNA appear to be needed compared with long dsRNA, consistent with the current hypothesis that dsRNA is processed into 21–23nt siRNA before degrading the target mRNA. Interestingly, we have shown that the level of inhibition of the EGFP expression is dependent on the amount of dsEGFP-RNA. Based on the current understanding of dsRNA processing, long dsRNA may be processed into 21–23nt siRNA to induce degradation of target mRNA in these neuronal cells, which may explain the higher efficiency of equal concentrations of long dsRNA compared to siRNA.

Materials and Methods

Materials and methods are as described in Example 4, except for the following:

Double-stranded RNA. The plasmid EGFP-C1 was used as template to produce PCR fragment corresponding to the full-length coding region and C-terminal fragment of EGFP. The PCR fragments were then subcloned in PCRTOPO4.0 plasmid. For in vitro transcription, the plasmid was linearized and transcribed with T3 and T7 RNA polymerase. Oligonucleotides used for PCR amplification for full-length EGFP ORF are (SEQ ID NO:17) ATGGTGAGCAAGGGC-GAGGAGCTG and (SEQ ID NO:18) TCTGAGTCCG-GACTTGTACAGCTC. dsRNA-EGFP and EGFP-C were 727 and 620 long, respectively. For annealing, equal molar of sense and antisense transcripts were heated at 60° C. for 3 minutes and cooled down at room temperature for more than 15 minutes. In addition, dsRNA preparation was treated with RNase T1 to eliminate any remaining ssRNA. The quality of the dsRNA preparations was analyzed on 1.2% native agarose gel. Sense and anti-sense UCP2 were generated from RNA derived from UCP2 were generated using T7 and SP6 polymerase respectively. The template used was a PCR fragment. UCP2 dsRNA was generated similarly as described.

EXAMPLE 7 dsRNA Inhibition of Endogenous Sequences

To test for RNAi-mediated gene silencing of endogenous genes, several types of genes were chosen, including genes involved in apoptotic pathways such as caspase-3, p53, 14-3-3, and kinases such as MAP kinase p38, fas-activated serine threonine kinase (FASTK), and housekeeping enzymes such as Homo-Coenzyme synthase 1. For quantification of changes in gene expression after dsRNA transfection, RT-PCR and real time PCR were used.

To generate dsRNAs corresponding to the above mouse genes, partial sequences of the mouse genes were cloned into PCR4.0TOPO (Invitrogene). The average length of the dsRNAs corresponding to the partial sequences of the above genes is about 600–800 bps. The table below shows the positions of the oligonucleotides used for cloning the PCR fragments, the length of each dsRNA, and the positions of the oligonucleotides used for quantification of the mRNA level after transfection.

TABLE 1 dsRNA-mediated inhibition of gene expression quantified with real-time PCR

| Gene name | Accession Number | dsRNA Region | % of knockdown[1] |
|---|---|---|---|
| mCaspase3 | NM_009810 | 2–723 | 87.3 ± 4.34 |
| mFAST | NM_023229 | 67–640 | 65.8 ± 7.34 |
| mP53 | M13873 | 102–881 | 65.7 ± 7.68 |
| mCoenzyme A synthase 1 | BC013443 | 174–583 | 73.7 ± 9.17 |
| m14-3-3 | D87663 | 284–774 | 98.7 ± 0.41 |
| mP38 | NM_011951 | 321–828 | 89.7 ± 4.34 |
| rP38[2] | | 1606–2204 | 85.0 ± 1.91 |

5 nM dsRNA was transfected into N2a cells. Three days after transfection, cells were harvested and total RNA was extracted for RT-PCR as described in Materials and Methods. As shown in FIGS. 9A–F, gene specific dsRNA induces profound silencing of the cognate mRNA while control dsRNA-EGFP shows little or no silencing effect. To test whether dsRNA induces non-specific silencing, we used GAPDH as our internal control. No difference in the expression levels of GAPDH was observed between dsRNA-transfected and mock-transfected, indicating that there was no non-specific silencing induced by long dsRNA in these mouse neuroblastoma cells under current experimental conditions (FIG. A–F).

Real time PCR was performed using an iCycler Real-Time detection system (Bio-Rad Laboratories, Hercules, Calif.) to quantitatively measure dsRNA-induced gene-specific silencing (above table). The efficiency of inhibition ranges from 65% to 98%, depending on the gene. These results further confirm that RNAi machinery is highly active in N2a cells and the silencing effects we observed at the protein level are not due to post-translational mechanisms, but are mediated at the transcriptional level.

It has previously been reported that dsRNA-induced inhibition appears to be transient when transfected into mammalian cells. The present experiments show dsRNA-induced inhibition that is both transient and time-dependent. Different genes require different lengths of post-transfection time for efficient inhibition of gene expression. For example, dsRNA-p53 induced maximal inhibition in 24–48 hours, while both dsRNA-PARP and dsRNA-EGFP induce maximal inhibition in 96 hours. This phenomena can be best explained by the fact that the mRNA and protein of different genes have different stability and turn over time. For example, EGFP is known to be much more stable than p53 protein, which has a typical half-life of 20 minutes.

The effective dsRNAs used so far all corresponded to full-length or portions of the open reading frame and shared 100% sequence identity with endogenous sequences. The question was then addressed whether effective dsRNA can only be derived from the ORF and whether 100% sequence identity is required for efficient silencing of the cognate message.

Figure 9B:
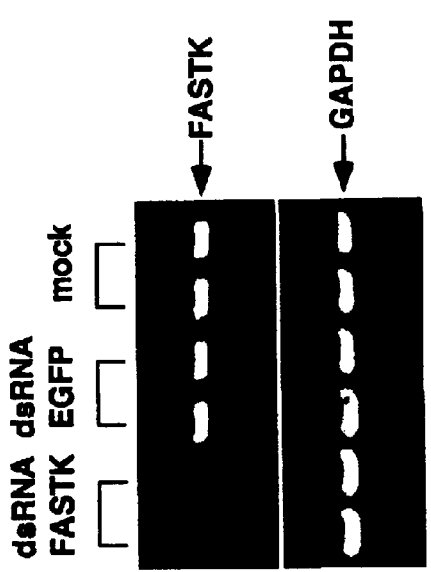
FIGS. 9A–9D show dsRNA-mediated inhibition of expression of caspase-3 (A), fas-activated kinase (FASTK, B), 14-4-3 (C) and 3-hydroxy-3-methylglutaryl-Coenzyme A synthase (D). Control level of each mRNA was determined in cells transfected with dsEGFP RNA and in mock transfected cells. Levels of GAPDH expression served as controls to ensure the quality of mRNA as well as equal amount of cDNA was used in each reaction.
Figure 9D:
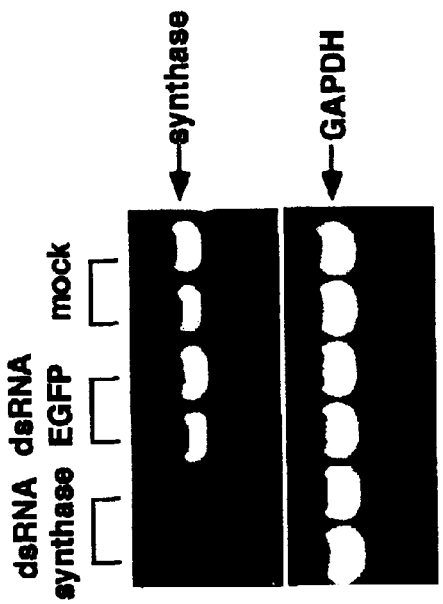
Figure 9A:
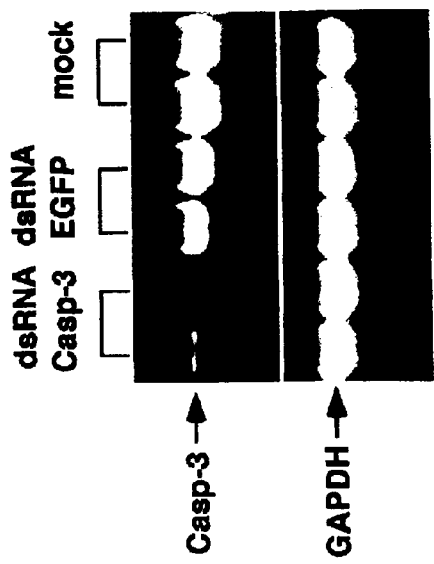
Figure 9C:
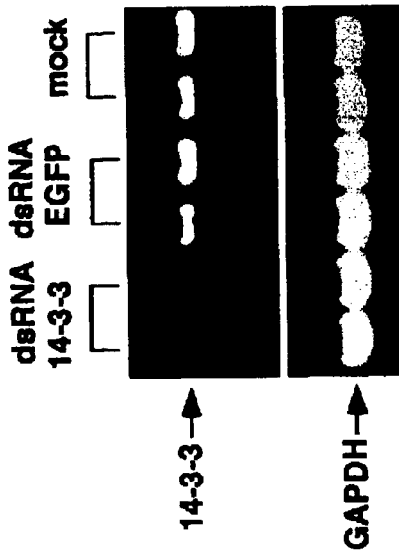

The present experiments show that dsRNA corresponding to the partial ORF of mouse p38 induces efficient silencing of p38 mRNA in mouse neuroblastoma N2a cells 9 (FIG. 9C). It was then tested whether dsRNA corresponding to the 3'UTR of the rat p38 gene (dsRNA-rat-p38), which shares about 80% identity with the mouse p38 gene sequence in that region, also can induce gene-specific silencing in N2a cells. Indeed, dsRNA-rat-p38 induces efficient silencing of p38 mRNA in N2a cells, indicating that effective dsRNA is not restricted to sequences in the ORF, and that 100% sequence identity is not required.

Recent studies show that long dsRNA induced gene-specific silencing in non-differentiated and embryonic cells. In our experiments, N2a cells undergo serum withdrawal, which induces partial differentiation. It was then tested whether RNAi is active in fully differentiated N2a cells. Cells were transfected with 5 nM dsRNA and then incubated in Neurobasal medium (Invitrogen) with N2 supplement (Invitrogen) in the presence of 20 $\mu$M retinoid acid to induce neuronal differentiation. After three days, N2a cells were fully differentiated with long processes. The proliferation rate decreased dramatically after 2–3 days in differentiation media, as measured with the amount of incorporated BrdU. Real-time PCR was then used to test whether long dsRNA can induce gene-specific silencing in these fully differentiated neuronal cells. The 14-3-3 mRNA level was inhibited by about 80% in differentiated cells transfected with ds14-3-3 RNA compared with cells transfected with dsEGFP (FIG. 10). These results indicate that RNAi is not restricted to non-differentiated cells or cells of embryonic origin, but active in these fully-differentiated neuronal cells.

Materials and Methods

Materials and methods are as described in Example 4, except for the following:

Quantitation of Expression. SYBR Green real-time PCR amplifications were performed in a iCycler Real-Time Detection System (Bio-Rad Laboratories, Hercules, Calif.). Primers were designed using Primer3 developed by the Whitehead Institute for Biomedical Research and the primers (Operon Technologies, Alameda, Calif.) concentrations were optimized for use with the SYBR green PCR master mix reagents kit. The sizes of the amplicons were checked by running out the PCR product on a 1.5% agarose gel. The thermal profile for all SYBR Green PCRs was 50° C. for 2 minutes and 95° C. for 10 minutes, followed by 45 cycles of 95° C. for 15 seconds, 60° C. for 30 seconds followed by 72° C. for 40 seconds. The standard curves are used to calculate the PCR efficiency of the primer set. As an endogenous reference we used glyceraldehydes-3-phosphate dehydrogenase (GAPDH), recently demonstrated to be a suitable control gene for studying brain injury with real-time RT-PCR. All PCR reactions performed in triplicates. Quantification was performed using the comparative cycle threshold (CT) method, where CT is defined as the cycle number at which fluorescence reaches a set threshold value. The target transcript was normalized to an endogenous reference (simultaneous triplicate GAPDH reactions), and relative differences were calculated using the PCR efficiencies.

DsRNA corresponding to FASTK, caspase-3, p53, 14-3-3, p38, and 3-hydroxy-3-methylglutaryl-Coenzyme A synthase (synthase) were generated as follows. Briefly, partial sequences of these mouse genes were cloned using RT-PCR and inserted into PCR4.0TOPO and serve as templates for in vitro transcription. The oligonucleotides used for PCR to generate partial clone of FASTK (accession #NM_023229) are (SEQ ID NO:19) GTCTCCACCACCCAGCTCCATG and (SEQ ID NO:20) AGATGCTGACGAGGGTACTGCA. The oligonucleotides used for PCR to generate partial clone of capspase-3 (accession #NM_009810) are (SEQ ID NO:21) TGGAGAACAACAAAACCTCAGTGG and (SEQ ID NO:22) CTGTTAACGCGAGTGAGAATGTGC. The oligonucleotides used for PCR to generate partial clone of p53 (accession #M13873) are (SEQ ID NO:23) ACCTCACTGCATGGACGATCTG and (SEQ ID NO:24) GCAGTTCAGGGCAAAGGACTTC. The oligonucleotides used for PCR to generate partial clone of 14-3-3 (accession #D87663) are (SEQ ID NO:25) CGGCAAATGGTTGAAACTGA and (SEQ ID NO:26) CCTGCAGCGCTTCTTTATTCT. The oligonucleotides used for PCR to generate partial clone of p38 (accession NM_011951) are (SEQ ID NO:27) GCAGGAGAGGCCCACGTTCT and (SEQ ID NO:28) CATCATCAGTGTGCCGAGCCA. The oligonucleotides used for PCR to generate partial clone of 3-hydroxy-3-methylglutaryl-Coenzyme A synthase 1 (accession #BC013443) are (SEQ ID NO:28) CGTGGTATCTGGTCAGAGTGGA and (SEQ ID NO:29) GCCAGACCACAACAGGAAGCAT. The oligonucleotides used for PCR to generate partial clone of all dsRNA used for transfections are blunt-ended.

The primers used to quantify caspase-3 are: (SEQ ID NO:30) GTACGCGCACAAGCTAGAAT and (SEQ ID NO:31) AAAGTGGAGTCCAGGGAGAAG; for FASTK, the primers are (SEQ ID NO:32) GGTGGTCAAAGGTTGGAAGT and (SEQ ID NO:33) CCATTACGTGAGGAGTCAGTTC; for p53, the primers are (SEQ ID NO:34) GCGTAAACGCTTCGAGATG and (SEQ ID NO:35) AGTAGACTGGCCCTTCTTGGT; for synthase, the primers are (SEQ ID NO:36) CTGGCCAGTGGTAAATGTACTG and (SEQ ID NO:37) CTCTGCCTTTTGCTGTCAGA; for 14-3-3, the primers are (SEQ ID NO:38) CGCTGTGGACCTCAGACAT and (SEQ ID NO:39) GGGGTAGTCAGAGATGGTTTCT; for p38, the primers are (SEQ ID NO:40) GTGGAAGAGCCTGACCTATGAT and (SEQ ID NO:41) CCCCTCACAGTGAAGTGAGATA.

For the purposes of clarity and understanding, the invention has been described in these examples and the above disclosure in some detail. It will be apparent, however, that certain changes and modifications may be practiced within the scope of the appended claims. All publications and patent applications listed herein are hereby incorporated by reference in their entirety for all purposes to the same extent as if each were so individually denoted.

What is claimed is:

1. A method for validating the effect of a candidate gene that is expressed in a mammalian neural or glial cell of interest, said method comprising:
   (a) producing a candidate dsRNA with a sequence identical to at least a portion of a said candidate gene;
   (b) introducing said candidate dsRNA into a reference mammalian neural or glial cell; and
   (c) validating the effect of said candidate gene by detecting an alteration in a cellular activity or a cellular state in said reference mammalian neural or glial cell, wherein said alteration is the result of specific attenuation of mRNA corresponding to said candidate in said reference mammalian neural or glial cell indicating that said candidate gene plays a functional role in mammalian neural or glial cells.

2. The method of claim 1, wherein said step of producing the candidate dsRNA comprises:
   (i) producing a cDNA corresponding to said candidate gene from an mRNA of said mammalian neural or glial cell of interest; and
   (ii) producing the candidate dsRNA from said cDNA.

3. The method according to claim 2, further comprising:
   producing a plurality of candidate cDNAs from said mammalian neural or glial cell of interest producing a plurality of candidate dsRNA with a sequence identical to at least a portion of said candidate cDNAs;

introducing each of the candidate dsRNA into a plurality of separate reference mammalian neural or glial cells having a gene expression similar said mammalian, neural or glial cell of interest; and validating the effect of said candidate genes by testing for alterations in a cellular activity or a cellular state in said reference mammalian neural glial cell that result from attenuation of mRNA corresponding to said candidate cDNA in said reference mammalian neural or glial cell, wherein detection of said alterations is indicative that said candidate gene plays a functional role in said mammalian neural or glial cells of interest.

4. The method of claim 3, wherein said step of producing a plurality of candidate cDNAs comprises:

producing a double-stranded cDNA from mRNA by reverse transcription;

producing cDNAs of a similar length by digesting said cDNA with a restriction enzyme; and producing a plasmid or PCR fragment from said cDNA after said digesting step.

5. The method of claim 4, wherein the candidate dsRNA is produced by transcribing said plasmid cDNA or PCR fragment.

6. The method of claim 4, wherein the restriction enzyme is selected from the group consisting of DpnI and RasI.

7. The method of claim 3, wherein said step of producing the plurality of candidate dsRNAs comprises:

selecting a candidate cDNA that is expressed at a detectably different level with respect to said reference mammalian neural or glial cell and said mammalian neural or glial cell of interest, and said reference mammalian neural or glial cell and said mammalian neural or glial cell of interest differ with a respect to cellular characteristic that is detectable by said step of testing for alterations in a cellular activity or a cellular state.

8. The method of claim 7, wherein the candidate cDNA is selected from a normalized library prepared from said reference mammalian neural or glial cells or said mammalian neural or glial cell of interest and is present in low abundance in the normalized library.

9. The method of claim 7, wherein the candidate cDNA is a differentially expressed cDNA gene selected from a subtracted library that is enriched for cDNAs that are differentially expressed with respect to said reference mammalian neural or glial cells or said mammalian neural or glial cell of interest.

10. The method of claim 7, wherein said step of selecting the candidate cDNA comprises:

preparing a tester-normalized cDNA library from test cells; a driver-normalized cDNA library from control cells; a tester-subtracted cDNA library which is enriched in one or more genes that are up-regulated with respect to the test cell and the control cell, and a driver-subtracted cDNA library which is enriched in one or more genes that are down-regulated with respect to the test cell and the control cell; and selecting a cDNA from the normalized libraries by contacting cDNAs from the tester-normalized cDNA library with labeled probes derived from mRNA from test cells and contacting cDNAs from the driver-normalized cDNA library with labeled probes derived from mRNA from control cells under conditions whereby probes specifically hybridize with complementary cDNAs to form a first set of hybridization complexes and detecting at least one hybridization complex from the first set of hybridization complexes to identify a cDNA that is present in low abundance.

11. The method of claim 7, wherein said step of selecting the candidate cDNA comprises:

preparing a tester-normalized cDNA library from test cells, a driver-normalized cDNA library from control cells; a tester-substracted cDNA library which is enriched in one or more genes that are up-regulated with respect to the test cell and the control cell, and a driver-substracted cDNA library which is enriched in one or more genes that are down-regulated with respect to the test cell and the control cell; and selecting a cDNA from the substracted libraries by contacting cDNAs from the tester-substracted cDNA library and contacting cDNAs from the driver-substracted cDNA library with a population of labeled probes under conditions whereby probes from the population of probes specifically hybridize with complementary cDNAs to form a second set of hybridization complexes, and wherein the population of labeled probes is derived from mRNA from test cells and control cells; and detecting at least one hybridization complex from the second set of hybridization complexes to identify a cDNA that is differentially expressed above a threshold level with respect to the subtracted libraries.

12. The method of claim 7, wherein the cellular characteristic is cell health, the test cell is a diseased neural or glial cell and the control cell is a healthy neural or glial cell, and the candidate gene is suspected of correlation with a disease.

13. The method of claim 12, wherein the test cell is obtained from a mammal that has had a stroke or is at risk for stroke.

14. The method of claim 7, wherein the cellular characteristic is cellular differention and the candidate gene is suspected of correlation with control of cellular differentiation.

15. The method of claim 7, wherein the candidate gene is endogenous to said mammalian neural or glial reference cell.

16. The method of claim 7, wherein the candidate gene is an extrachromosomal gene in said mammalian neural or glial reference cell.

17. The method of claim 12, wherein the said mammalian neural or glial reference cell is a neuroblastoma cell.

18. The method of claim 17, wherein said mammalian neural or glial reference cell has increased sensitivity by N-methyl-D-aspartate, β-amyloid, peroxide, oxygen-glucose deprivation, or combinations thereof relative to a normal mammalian neural or glial cell.

19. The method of claim 18, wherein the detecting step comprises detecting a decrease in cellular sensitivity to N-methyl-D-aspartate, β-amyloid peroxide, oxygen-glucose deprivation, or combinations thereof relative to a normal mammalian neural or glial cell.

20. The method of claim 3, wherein the detecting step comprises detecting modulation of ligand binding to a protein.

21. The method of claim 1, wherein the determining step comprises determining whether the protein encoded by the candidate gene binds to another protein to form a complex.

* * * * *